(12) United States Patent
Hsu

(10) Patent No.: US 7,087,390 B2
(45) Date of Patent: Aug. 8, 2006

(54) CAIP-LIKE GENE FAMILY

(75) Inventor: Yen-Ming Hsu, Lexington, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 339 days.

(21) Appl. No.: 10/144,621

(22) Filed: May 13, 2002

(65) Prior Publication Data

US 2002/0172671 A1 Nov. 21, 2002

Related U.S. Application Data

(60) Division of application No. 08/671,354, filed on Jun. 27, 1996, now Pat. No. 6,423,824, which is a continuation-in-part of application No. 08/484,710, filed on Jun. 7, 1995, now Pat. No. 5,656,438, and a continuation-in-part of application No. 08/475,894, filed on Jun. 7, 1995, now Pat. No. 5,641,748, and a continuation-in-part of application No. 08/484,709, filed on Jun. 7, 1995, now Pat. No. 5,837,844, and a continuation-in-part of application No. 08/474,697, filed on Jun. 7, 1995, now Pat. No. 6,171,800, and a continuation-in-part of application No. 08/486,344, filed on Jun. 7, 1995, now abandoned.

(51) Int. Cl.
C07K 14/435 (2006.01)
G01N 33/53 (2006.01)

(52) U.S. Cl. .................. 435/7.1; 435/7.2; 530/300; 530/350

(58) Field of Classification Search .................. 435/7, 435/7.1, 7.2, 7.21, 6; 436/501; 530/300, 530/350
See application file for complete search history.

(56) References Cited

U.S. PATENT DOCUMENTS 5,525,503 A 6/1996 Rudd et al.

FOREIGN PATENT DOCUMENTS

| WO | WO 90/13644 | 9/1990 |
| WO | WO 95/07981 | 3/1995 |
| WO | WO 95/34646 | 12/1995 |

OTHER PUBLICATIONS

Barclay et al., 1997, The Leucocyte Antigen FactsBook, 2nd Ed. (Academic Press Harcourt Brace &Comp.:San Diego) p. 134-136.*
Bierer et al., "Partial deletions of the cytoplasmic domain of CD2 result in a partial defect in signal transduction," Journal of Immunology, vol. 144, No. 3, 785-789 (1990).
Bromberg, "The Biology of CD2: Adhesion, Transmembrane Signal, and Regulatory Receptor of Immunity," Journal of Surgical Research, vol. 54, 258-267 (1993).
Carmo et al., "Physical association of the cytoplasmic domain of CD2 with the tyrosine kinases p56$^{lck}$ and p 59$^{fyn}$," Eur. J. Immunol., vol. 23, 2196-2201 (1993).
Carrera et al., "CD2 is involved in regulating cyclic AMP levels in T cells," Eur. J. Immunol., vol. 18, 961-964 (1988).
Chang et al., "Dissection of the human CD2 intracellular domain," J. Exp. Med., vol. 169, 2073-2083 (1989).
Dayhoff et al., "A Model of Evolutionary Change in Proteins," Atlas of Protein Sequence and Structure, Chp. 22, 345-352 (1978).
Donovan, et al., "Restoration of CD2-Mediated Signaling by Chimeric Membrane Protein Including the Cytoplasmic Sequence of CD45," Human Immunology, vol. 40, 123-130 (1994).
Franco et al., "Regulation of CD2-Mediated Human T Cell Activation: Anti-CD8 Monoclonal Antibodies Inhibit CD2-Mediated Rise in Intracellular Calcium," Cellular Immunology, vol. 152, 162-175 (1993).
Gassmann et al., "Identification of a signaling complex involving CD2, ζ chain and p59$^{fyn}$ in T lymphocytes," Eur. J. Immunol., vol. 24, 139-144 (1994).
Hahn, et al., "A distinct cytoplasmic domain of CD2 regulates ligand avidity and T-cell responsiveness to antigen," Proc. Natl. Acad. Sci. USA., vol. 89, 7179-7183 (1992).
Hahn et al., "Signal Transduction Pathways Involved in T Cell Receptor-Induced Regulation of CD2 Avidity for CD58$^1$," Journal of Immunology, vol. 150, No. 7, 2607-2619 (1993).
He et al., "A Role in Transmembrane Signaling for the Cytoplasmic Domain of the CD2 T Lymphocyte Surface Antigen," Cell, vol. 54, 979-984 (1988).
Hein, "Unified Approach to Alignment and Phylogenies," Methods in Enzymology, vol. 183, 626-645 (1990).
Koch et al., "SH2 and SH3 Domains: Elements That Control Interactions of Cytoplasmic Signaling Proteins," Science, vol. 252, 668-674 (1991).
Kozarsky et al., "An Anti-CD2 Monoclonal Antibody That Both Inhibits and Stimulates T Cell Activation Recognizes a Subregion of CD2 Distinct from Known Ligand-Binding Sites," Cellular Immunology, vol. 150, 235-246 (1993).
Moingeon et al., "The Structural Biology of CD2," Immunological Reviews, No. 111, 111-144 (1989).
Offringa and Bierer, "Association of CD2 with Tubulin," Journal Biological Chemistry, vol. 268, No. 7, 4979-4988 (1993).
Saitou and Nei, "The Neighbor-joining Method: A New Method for Reconstructing Phylogenetic Trees," Mol. Biol. Evol., vol. 4(4), 406-425 (1987).
Sato et al., "Cytoplasmic Membrane-Associated Protein (CAP) Isolated from Streptococcus pyogenes: As a New Bacterial Superantigen," Microbiol. Immunol., vol. 38(2), 139-147 (1994).

(Continued)

Primary Examiner—Lorraine Spector
Assistant Examiner—Claire M. Kaufman
(74) Attorney, Agent, or Firm—Fish & Richardson P.C.

(57) ABSTRACT

CAIP polypeptide, nucleic acids, ands uses thereof.

9 Claims, 3 Drawing Sheets

OTHER PUBLICATIONS

Schlessinger, "SH2/SH3 signaling proteins: Oncogenes and cell proliferation," Current Opinion in Genetics and Development, vol. 4, 25-30 (1994).

Schwartz and Dayhoff, "Matrices for Detecting Distant Relationships," in *Atlas of Protein Sequence and Structure*, Chp. 23, 353-357 (1978).

Suthanthiran, "Transmembrane signalling via the T cell antigen receptor heterodimer and the CD2 antigen," *Transplantation*, vol. 47, No. 2, 348-351 (1989).

Wilbur and Lipman, "Rapid similarity searches of nucleic acid and protein data banks," *Proc. Natl. Acad. Sci. USA*, vol. 80, 726-730 (1983).

Database EMBL En961102, AN aa100099 Sequence HSAA99 from human cDNA clone 525921 5'.

Abraham, K.M. et al. "Delayed Thymocyte Development Induced by Augmented Expression of p56$^{lck}$" *J. Exp. Med.* *173*:1421-1432 (Jun. 1991).

Bartel, P.L. et al. "Using the two-hybrid system to detect protein-protein interactions" in *Cellular Interaction in Development: A Practical Approach*, D.A. Hartley, ed. (Oxford: Oxford University Press, 1993):153-179.

Bell, G.M. et al. "The SH3 Domain of p56$^{lck}$ Binds to Proline-rich Sequences in the Cytoplasmic Domain of CD2" *J. Exp. Med. 183*:169-178 (Jan. 1996).

Hall, J.L. et al. "Identification of Two-Human β-Tubulin Isotypes" *Mol. Cell. Biol. 3*(5):854-862 (May 1983).

Ramos-Morales, F. et al. "P56$^{lck}$: A Transducing Protein That Binds to SH2 Containing Proteins and to Phosphotyrosine Containing Proteins" *Cell. Mol. Biol. 40*(5):695-700 (1994).

Ramos-Morales, F. et al. "Vav binds to several SH2/SH3 containing proteins in activated lymphocytes" *Oncogene 9*(7):1917-1923 (1994).

Reeck, G.R. et al. "Homology in Proteins and Nucleic Acids: A Terminolgy Muddle and a Way out of It" *Cell 50*:667 (Aug. 27, 1987).

\* cited by examiner

DNA sequence of YM06

```
TGCAATAGCAAAGTACCCACAAACCGGGTGGTACTGGGTACTGTGGGTTGTCCCGCAGTTCTG
GAGGCTGGAAGTCTGAAACTCAGATGCTGGCAGGGTTAATTTGTCCTGAGGGCTGTGAGGGAG
ACACAGCTCCTGGCTTTCTCCTAGCTGCTGGTAGTTTACTGGCAACCTTTGGCATTCCTTAGCTT
GTGGCATCATCACTCCAGTATTCATGTGATATTCTTCCTGTGTGTGTGTCTCTATGTCAAGATTT
CCCCTGTTTATAACAAAACCAXTCATATTGGGTTAGTGGTTGAGCCCACCTTACTGACCAAATA
AAGTCACATGTCGAGGTACTACGGGTTAGGATTTCAACATGTACATTTTAGAGGGACACAATT
TAATCTATAATAGTGTGGAATTTTCTTTTGGGTATCTACCAGTCACCAAGATATTTATCCCTACT
TGACCAGGCACGATGATGAGCTXACGATCAGCGTGGGTGAAATCATCACCAACATCAGGAAG
GAGGATGGAXGCTGGTGGGAGGGACAGATCAACGGCAGGAGAGGTTTGTTCCCTGACAACTT
TGTAAGAGAAATAAAGAAAGAGATGAAGAAAGACCCTCTCACCAACAAAGCTCCAGAAAAGC
CCCTGCACGAAGTGCCCAGTGGAAACTCTTTGCTGTCTTCTGAAACGATTTTAAGAACCAATAA
GAGAGGCGAGCGACGGAGGCGCCGGTGCCAGGTGGCATTCAGCTACCTGCCCCAGAATGACG
ATGAACTTGAGCTGAAAGTTGGCGACATCATAGAGGTGGTAGGAGAGGTAGAGGAAGGATGG
TGGGAAGGTGTTCTCAACGGGAAGACTGGAATGTTTCCTTCCAACTTCATCAAGGAGCTGTCA
GGGGAGTCGGATGAGCTTGGCATTTCCCAGGATGAGCAGCTATCCAAGTCAAGTTTAAGGGAA
ACCACAGGCTCCGAGAGTGATGGGGGTGACTCAAGCAGCACCAAGTCTGAAGGTGCCAACGG
GACAGTGGCAACTGCAGCAATCCAGCCCAAGAAAGTTAAGGGAGTGGGCTTTGGAGACATTTT
CAAAGACAAGCCAATCAAACTAAGACCAAGGTCAATTGAAGTAGAAAATGACTTTCTGCCGGT
AGAAAAGACTATTGGGAAGAAGTTACCTGCAACTACAGCAACTCCAGACTCATCAAAAACAG
AAATGGACAGCAGGACAAAGAGCAAGGATTACTGCAAAGTAATATTTCCATATGAGGCACAG
AATGATGATGAATTGACAATCAAAGAAGGAGATATAGTCACTCTCATCAATAAGGACTGCATC
GACGTAGGCTGGTGGGAAGGAGAGCTGAACGGCAGACGAGGCGTGTTCCCCGATAACTTCGT
GAAGTTACTTCCACCGGACTTTGAAAAGGAAGGGAATAGACCCAAGAAGCCACCGCCTCCATC
CGCTCCTGTCATCAAACAAGGGGCAGGCACCACTGAGAGAAAACATGAAATTAAAAAGATAC
CTCCTGAAAGACCAGAAATGCTTCCAAACAGAACAGAAGAAAAAGAAAGACCAGAGAGAGA
GCCAAAACTGGATTTACAGAAGCCCTCCGTTCCTGCCATACCGCCAAAAAAGCCTCGGCCACC
TAAGACCAATTCTCTCAGCAGACCTGGCGCACTGCCCCCGAGAAGGCCGGAGAGACCGGTGGG
TCCGCTGACACACACCAGGGGTGACAGTCCAAAGATTGACTTGGCCGGCAGTTCGCTATCTGG
CATCCTGGACAAAGATCTCTCGGACCGCAGCAATGACATTGACTTAGAAGGTTTTGACTCCGT
GGTATCATCTACTGAGAAACTCAGTCATCCGACCACAAGCAGACCAAAAGCTACAGGGAGGC
GGCCTCCGTCCCAGTCCCTCACATCTTCATCCCTTTCAAGCCCTGATATCTTCGACTCCCCAAGT
CCCGAAGAGGATAAGGAGGAACACATTTCACTTGCGCACAGAGGAGTGGACGCGTCAAAGAA
AACTTCCAAGACTGTTACCATATCCCAAGTGTCTGACAACAAAGCATCCCTGCCGCCCAAGCC
GGGGACCATGGCAGCAGGTGGCGGTGGGCCAGCCCCTCTGTCCTCAGCGGCGCCCTCCCCCCT
GTCATCCTCTTTGGGAACAGCTGGACACAGAGCCAACTCCCCGTCTCTGTTCGGCACGGAAGG
AAAACCAAAGATGGAGCCTGCGGCCAGCAGCCAGGCGGCCGTGGAGGAGCTAAGGACACAGG
TCCGCGAGCTGAGGAGCATCATCGAGACCATGAAGGACCAGCAGAAACGAGAGATTAAACAG
TTATTGTCTGAGTTGGATGAAGAGAAGAAAATCCGGCTTCGGTTGCAGATGGAAGTGAACGAC
ATAAAGAAAGCTCTACAATCAAAATGAATACTTGATCAATGAAATGTCACATTATTCATCCTG
AGTCCGAGACTCAAATTTTCTGCCCAGCCAAAATAATCTTGTGCCAAAAGATTAAAGGTTTGC
CTCAAAATGTCCCTGTTTGAAAGATTAGCACAAAAGTCTTGATAGCACAACACAAATTCCATC
CAAGAGGAGAATCTTCCCCAGGGTTTAGTCCTGGGGCTGGCACTCGTTGTGACTTACACAGAG
CAAAATTGTGCTAAAGGCTTTTCTACTCTGAGATCTCAATGCGAAATGAAAACTCAGGCAGTTT
AGTCCATAGTGGTACTATTTTGATGATATTTTCCATTAATAAAATGTAATTTCAGATTATTCGTT
TACAAGCTTTATAATTTTXTGATTTTXTAATCGTGTTTTGTCACAGACTTCCCTAGTGTTTGTAC
TACACGTAGTCAGAAGCGAGTGTCCTTTTCTTTTGCTTCAGGCTAAGAGCTGCCTCGCTCTTTG
TCCCCCATTAGGATTCTATTACATATGCAATTGTAGGTTCAACCTGTCCCTTTCCCTGCCAGCA
AACCCCACCACCCTAAGAGAAATTTTAGCTTATATATGACGGTATATTTACAAAAAGAGAAAG
AGAAAATCTGGTATTTGCAATGATCTGTGCCTTCTTTTACCACCCTCTTGATTGGAGCTTTTGT
GATGCAGCTACCATGATTCAAAAAAATGCGGCCGCGCTCGAGCTCGAATTC (SEQ ID NO:1)
```

FIGURE 1

SH3 domains and potential SH3-binding domains of YM06 (659 aa)

SH3-1
IYPYLTRHDDELTISVGEIITNIRKEDGXWWEGQINGRRGLFPDNFVREIKKE

MKKDPLTNKAPEKPLHEVPSGNSLLSSETILRTNKRGERRRRRCQVAFSYLPQND

SH3-2
DELELKVGDIIEVVGEVEEGWWEGVLNGKTGMFPSNFIKELSGESDELGISQDEQ

LSKSSLRETTGSESDGGDSSSTKSEGANGTVATAAIQPKKVKGVGFGDIFKDKPIK

LRPRSIEVENDFLPVEKTIGKKLPATTATPDSSKTEMDSRTKSKDYCKVIFPYEAQ

SH3-3
NDDELTIKEGDIVTLINKDCIDVGWWEGELNGRRGVFPDNFVKLLPPDFEKEGNR

HP-1                  HP-2
PKKPPPPSAPVIKQGAGTTERKHEIKKIPPERPEMLPNRTEEKERPEREPKLDLQKP

HP-3             HP-4
SVPAIPPKKPRPPKTNSLSRPGALPPRRPERPVGPLTHTRGDSPKIDLAGSSLSGILD

KDLSDRSNDIDLEGFDSVVSSTEKLSHPTTSRPKATGRRPPSQSLTSSSLSSPDIFDS

PSPEEDKEEHISLAHRGVDASKKTSKTVTTSQVSDNKASLPPKPGTMAAGGGGP

APLSSAAPSPLSSSLGTAGHRANSPSLFGTEGKPKMEPAASSQAAVEELRTQVRE

LRSIIETMKDQQKREIKQLLSELDEEKKIRLRLQMEVNDIKKALQSK (SEQ ID NO:2)

FIGURE 2

CAIP-LIKE GENE FAMILY

This application is a divisional of U.S. Ser. No. 08/671,354, filed June 27, 1996 now U.S. Pat. No. 6,423,824, which is a continuation-in-part of: U.S. Ser. No. 08/484,710, filed Jun. 7, 1995, now U.S. Pat. No. 5,656,438; U.S. Ser. No. 08/475,894, filed Jun. 7, 1995, now U.S. Pat. No. 5,641,748; U.S. Ser. No. 08/484,709, filed Jun. 7, 1995, now U.S. Pat. No. 5,837,844; U.S. Ser. No. 08/474,697, filed Jun. 7, 1995, now U.S. Pat. No. 6,171,800; and U.S. Ser. No. 08/486,344, filed Jun. 7, 1995, now abandoned, all of which are hereby incorporated by reference.

BACKGROUND OF THE INVENTION

The invention relates to CAIP gene, and other related genes, their products, and uses thereof.

SUMMARY OF THE INVENTION

The inventor has discovered novel intracellular lymphocyte proteins. These proteins are termed, CAIP's, for "CD2 Associated Intracellular Proteins". The CAIP's, thus discovered, can interact with the intracellular domain of CD2.

Accordingly, the invention features, a recombinant polypeptide or substantially pure preparation of a peptide, the sequence of which includes, or is, the sequence of a CAIP polypeptide.

In preferred embodiments: the polypeptide has biological activity, e.g., it specifically binds a CD2 intracellular domain; the polypeptide includes an amino acid sequence at least 60%, 80%, 90%, 95%, 98%, or 99% homologous to an amino acid sequence from SEQ ID NO:2; the polypeptide includes an amino acid sequence essentially the same as an amino acid sequence in SEQ ID NO:2; the polypeptide is at least 5, 10, 20, 50, 100, or 150 amino acids in length; the polypeptide includes at least 5, preferably at least 10, more preferably at least 20, most preferably at least 50, 100, or 150 contiguous amino acids from SEQ ID NO:2; the CAIP polypeptide is either, an agonist or an antagonist, of a biological activity of a naturally occurring CAIP. For example, the CAIP polypeptide is an agonist or antagonist of CAIP-CD2 binding or of CAIP or CD2-mediated intracellular signaling.

In a preferred embodiment, the subject CAIP polypeptide differs in amino acid sequence at 1, 2, 3, 5, 10 or more residues, from a sequence in SEQ ID NO:2. The differences, however, are such that: the CAIP polypeptide exhibits a CAIP biological activity, e.g., the CAIP polypeptide retains a biological activity of a naturally occurring CAIP, e.g., the CAIP polypeptide from SEQ ID NO:2.

In preferred embodiments the CAIP polypeptide includes a CAIP sequence described herein as well as other N-terminal and/or C-terminal amino acid sequence.

In preferred embodiments, the polypeptide includes all or a fragment of an amino acid sequence from SEQ ID NO:2, fused, in reading frame, to additional amino acid residues, preferably to residues encoded by genomic DNA 5' to the genomic DNA which encodes a sequence from SEQ ID NO:2.

In yet other preferred embodiments, the CAIP polypeptide is a recombinant fusion protein having a first CAIP portion and a second polypeptide portion, e.g., a second polypeptide portion having an amino acid sequence unrelated to CAIP. The second polypeptide portion can be, e.g., any of glutathione-S-transferase, a DNA binding domain, or a polymerase activating domain. In preferred embodiment the fusion protein can be used in a two-hybrid assay.

In a preferred embodiment the CAIP polypeptide encodes amino acid residues 1–659; 1–47; 96–146; 265–317; 330–337; 358–367; 393–400; or 412–419 from SEQ ID NO:2.

In preferred embodiments the CAIP polypeptide has antagonistic activity, and is capable of: inhibiting CD2/CAIP binding, inhibiting CD2 or CAIP mediated intracellular signaling, inhibiting lymphocyte proliferation, e.g., T cell proliferation, or inhibiting an immune disorder characterized by unwanted T cell proliferation, e.g., as in psoriasis or unwanted rejection of transplant tissue.

In a preferred embodiment, the CAIP polypeptide is a fragment of a naturally occurring CAIP which inhibits the CD2 mediated intracellular signaling.

Polypeptides of the invention include those which arise as a result of the existence of multiple genes, alternative transcription events, alternative RNA splicing events, and alternative translational and postranslational events.

The invention includes an immunogen which includes a CAIP polypeptide in an immunogenic preparation, the immunogen being capable of eliciting an immune response specific for said CAIP polypeptide, e.g., a humoral response, an antibody response, or a cellular response. In preferred embodiments, the immunogen comprising an antigenic determinant, e.g., a unique determinant, from a protein represented by SEQ ID NO:2.

The present invention also includes an antibody preparation specifically reactive with an epitope of the CAIP immunogen or generally of a CAIP polypeptide, preferably an epitope which consists all or in part of residues from an SH3 domain, or an SH3 binding domain.

In preferred embodiments the CAIP-like polypeptide, as expressed in the cells in which it is normally expressed or in other eukaryotic cells, has a molecular weight of at least about 30 kDa, preferably at least about 40 kDa, more preferably at least about 50 kDa, as determined by SDS-PAGE.

Also included in the invention is a composition which includes a CAIP-like polypeptide and one or more additional components, e.g., a carrier, diluent, or solvent. The additional component can be one which renders the composition useful for in vitro, in vivo, pharmaceutical, or veterinary use.

In another aspect, the invention provides a substantially pure nucleic acid having or comprising a nucleotide sequence which encodes a polypeptide, the amino acid sequence of which includes, or is, the sequence of a CAIP polypeptide. In preferred embodiments: the encoded polypeptide has biological activity, e.g., it specifically binds a CD2 intracellular domain; the encoded polypeptide includes an amino acid sequence at least 60%, 80%, 90%, 95%, 98%, or 99% homologous to an amino acid sequence from SEQ ID NO:2; the encoded polypeptide includes an amino acid sequence essentially the same as an amino acid sequence in SEQ ID NO:2; the encoded polypeptide is at least 5, 10, 20, 50, 100, or 150 amino acids in length; the encoded polypeptide includes at least 5, preferably at least 10, more preferably at least 20, most preferably at least 50, 100, or 150 contiguous amino acids from SEQ ID NO:2; the encoded CAIP polypeptide is either, an agonist or an antagonist, of a biological activity of a naturally occurring CAIP. For example, the encoded CAIP polypeptide is an agonist or antagonist of the CAIP-CD2 binding or of CAIP or CD2-mediated intracellular signaling.

In preferred embodiments: the nucleic acid is or includes that of SEQ ID NO:1; the nucleic acid is at least 60%, 70%, 80%, 90%, 95%, 98%, or 99% homologous with a nucleic acid sequence from SEQ ID NO:1; the nucleic acid includes a fragment of SEQ ID NO:1 at least 25, 50, 100, 200, 300, 400, 500, or 1,000 bases in length.

In preferred embodiments the encoded polypeptide has antagonistic activity, and is preferably capable of: inhibiting CD2/CAIP binding, inhibiting CD2 or CAIP mediated intracellular signaling, inhibiting lymphocyte proliferation, e.g., T cell proliferation, or inhibiting an immune disorder characterized by unwanted T cell proliferation, e.g., as in psoriasis or unwanted rejection of transplant tissue.

In a preferred embodiment, the encoded CAIP polypeptide differs in amino acid sequence at 1, 2, 3, 5, 10 or more residues, from a sequence in SEQ ID NO:2. The differences, however, are such that: the CAIP encoded polypeptide exhibits a CAIP biological activity, e.g., the encoded CAIP polypeptide retains a biological activity of a naturally occurring CAIP, e.g., the CAIP polypeptide of SEQ ID NO:2.

In preferred embodiments, the encoded polypeptide includes all or a fragment of an amino acid sequence from SEQ ID NO:2, fused, in reading frame, to additional amino acid residues, preferably to residues encoded by genomic DNA 5' to the genomic DNA which encodes a sequence from SEQ ID NO:2.

In preferred embodiments the encoded CAIP polypeptide includes a CAIP sequence described herein as well as other N-terminal and/or C-terminal amino acid sequence.

In preferred embodiments, the polypeptide includes all or a fragment of an amino acid sequence from SEQ ID NO:2, fused, in reading frame, to additional amino acid residues, preferably to residues encoded by genomic DNA 5' to the genomic DNA which encodes a sequence from SEQ ID NO:2.

In yet other preferred embodiments, the encoded polypeptide is a recombinant fusion protein having a first CAIP portion and a second polypeptide portion, e.g., a second polypeptide portion having an amino acid sequence unrelated to the CAIP. The second polypeptide portion can be, e.g., any of glutathione-S-transferase; a DNA binding domain; or a polymerase activating domain. In preferred embodiments the fusion protein can be used in a two-hybrid assay.

In preferred embodiments, the subject CAIP nucleic acid will include a transcriptional regulatory sequence, e.g. at least one of a transcriptional promoter or transcriptional enhancer sequence, operably linked to the CAIP gene sequence, e.g., to render the CAIP gene sequence suitable for use as an expression vector.

In yet a further preferred embodiment, the nucleic acid which encodes a CAIP polypeptide of the invention, hybridizes under stringent conditions to a nucleic acid probe corresponding to at least 12 consecutive nucleotides from SEQ ID NO:1, more preferably to at least 20 consecutive nucleotides from SEQ ID NO:1, more preferably to at least 40 consecutive nucleotides from SEQ ID NO:1.

In a preferred embodiment the CAIP encoding nucleic acid sequence encodes amino acid residues 1–659; 1–47; 96–146; 265–317; 330–337; 358–367; 393–400; or 412–419 from SEQ ID NO:2.

In a preferred embodiment, the nucleic acid encodes a peptide which differs by at least one amino acid residue from a region of 1–659 from SEQ ID NO:2.

In a preferred embodiment, the nucleic acid differs by at least one nucleotide from a nucleotide sequence which encodes amino acids 1–659 from SEQ ID NO:1.

In another aspect, the invention includes: a vector including a nucleic acid which encodes a CAIP-like polypeptide, e.g., a CAIP polypeptide; a host cell transfected with the vector; and a method of producing a recombinant CAIP-like polypeptide, e.g., a CAIP polypeptide; including culturing the cell, e.g., in a cell culture medium, and isolating the CAIP-like polypeptide, e.g., a CAIP polypeptide, e.g., from the cell or from the cell culture medium.

In another aspect, the invention features, a purified recombinant nucleic acid having at least 50%, 60%, 70%, 80%, 90%, 95%, 98%, or 99% homology with a sequence from SEQ ID NO:1.

The invention also provides a probe or primer which includes or comprises a substantially purified oligonucleotide. The oligonucleotide includes a region of nucleotide sequence which hybridizes under stringent conditions to at least 10 consecutive nucleotides of sense or antisense sequence from SEQ ID NO:1, or naturally occurring mutants thereof. In preferred embodiments, the probe or primer further includes a label group attached thereto. The label group can be, e.g., a radioisotope, a fluorescent compound, an enzyme, and/or an enzyme co-factor. Preferably the oligonucleotide is at least 10 and less than 20, 30, 50, 100, or 150 nucleotides in length.

The invention involves nucleic acids, e.g., RNA or DNA, encoding a polypeptide of the invention. This includes double stranded nucleic acids as well as coding and antisense single strands.

In preferred embodiments, the encoded CAIP-like polypeptide, as expressed in the cells in which it is normally expressed or in other eukaryotic cells, has a molecular weight of at least about 30 kDa, preferably at least about 40 kDa, more preferably at least about 50 kDa, as determined by SDS-PAGE.

The inventor has discovered a representative of CAIP family of genes, the CAIP family being the first known members of the larger family of CAIP-like genes. The CAIP family of genes encodes products which interact with CD2. Other members of the CAIP-like family encode products which interact with the intracellular domain of cell surface molecules, but not necessarily with CD2. The CAIP-like family genes are thought to encode signal transducing proteins and as such interact with intracellular domains of cell surface molecules, as well as, with downstream molecules, e.g., intracellular downstream molecules.

Accordingly, the invention features a purified preparation of a CAIP-like family polypeptide, or a recombinant CAIP-like family peptide, having one or more of the following characteristics:

(i) the CAIP-like family polypeptide includes at least one CAIP-like-SH3 domain having at least 30, 40, 42, 50, 60, 70, 80, 90 or 95% sequence similarity with one of SH3 domain 1, SH3 domain 2, or SH3 domain 3 of SEQ ID NO:2, preferably in the N-terminal region) of the protein;
(ii) the CAIP-like family polypeptide lacks an SH2 domain;
(iii) the CAIP-like family polypeptide does not have kinase activity;
(iv) the CAIP-like family polypeptide preferably has at least one SH3 binding domain, preferably in the C-terminal (half or third) of the protein;
(v) the CAIP-like family polypeptide has an overall sequence similarity of at least 50%, preferably at least 60%, more preferably at least 70, 80, 90, or 95%, with a polypeptide of SEQ ID NO:2.

In preferred embodiments, the CAIP-like family polypeptide includes: 1, 2, 3 or more CAIP-like-SH3 domains and 1, 2, 3, 4 or more SH3 binding domains.

In preferred embodiments, the CAIP-like family polypeptide can form intramolecular interactions between an N-terminal CAIP-like-SH3 domain, e.g., SH3 domain 1, SH3 domain 2, or SH3 domain 3, and a C-terminal SH3 binding domain, e.g., SH3 binding domain 1, SH3 binding domain 2, SH3 binding domain 3, or SH3 binding domain 4.

In preferred embodiments, the CAIP-like polypeptide binds with the intracellular domain of a lymphocyte cell surface molecule, e.g., the intracellular domain of a lymphocyte cell surface molecule other than CD2, and/or with the downstream intracellular protein.

In preferred embodiments the CAIP-like polypeptide, as expressed in the cells in which it is normally expressed or in other eukaryotic cells, has a molecular weight of at least about 30 kDa, preferably at least about 40 kDa, more preferably at least about 50 kDa, as determined by SDS-PAGE.

In another aspect, the invention features a substantially pure CAIP nucleic acid which encodes a CAIP-like family polypeptide having one or more of the following characteristics:
(i) the CAIP-like family polypeptide includes at least one CAIP-like-SH3 domain having at least 30, 40, 42, 50, 60, 70, 80, 90, or 95% sequence similarity with one of SH3 domain 1, SH3 domain 2, or SH3 domain 3, of SEQ ID NO:2, preferably in the N-terminal region of the protein;
(ii) the CAIP-like family polypeptide lacks an SH2 domain;
(iii) the CAIP-like family polypeptide does not have kinase activity;
(iv) the CAIP-like family polypeptide preferably has at least one SH3 binding domain, preferably in the C-terminal (half or third) of the protein;
(v) the CAIP-like family polypeptide has an overall sequence similarity of at least 50%, preferably at least 60%, more preferably at least 70, 80, 90, or 95%, with a polypeptide of SEQ ID NO:2.

In preferred embodiments, the CAIP-like family polypeptide includes: 1, 2, 3 or more CAIP-like-SH3 domains and 1, 2, 3, 4 or more SH3 binding domains.

In preferred embodiments, the CAIP-like family polypeptide can form intramolecular interactions between an N-terminal CAIP-like-SH3 domain, e.g., SH3 domain 1, SH3 domain 2, or SH3 domain 3, and a C-terminal SH3 binding domain, e.g., SH3 binding domain 1, SH3 binding domain 2, SH3 binding domain 3, or SH3 binding domain 4.

In preferred embodiments, the CAIP-like polypeptide binds with the intracellular domain of a lymphocyte cell surface molecule, e.g., the intracellular domain of a lymphocyte cell surface molecule other than CD2, and/or with the downstream intracellular protein.

In preferred embodiments the CAIP-like polypeptide, as expressed in the cells in which it is normally expressed or in other eukaryotic cells, has a molecular weight of at least about 30 kDa, preferably at least about 40 kDa, more preferably at least about 50 kDa, as determined by SDS-PAGE.

In another aspect, the invention features a cell or purified preparation of cells which include a CAIP-like transgene, e.g., a CAIP transgene, or which otherwise misexpress a CAIP-like gene, e.g., a CAIP gene. The cell preparation can consist of human or non human cells, e.g., rodent cells, e.g., mouse or rat cells, rabbit cells, or pig cells. In preferred embodiments, the cell or cells include a CAIP transgene, e.g., a heterologous form of a CAIP gene, e.g., a gene derived from humans (in the case of a non-human cell). The CAIP transgene can be misexpressed, e.g., overexpressed or underexpressed. In other preferred embodiments, the cell or cells include a gene which misexpress an endogenous CAIP gene, e.g., a gene the expression of which is disrupted, e.g., a knockout. Such cells can serve as a model for studying disorders which are related to mutated or mis-expressed CAIP alleles or for use in drug screening.

In another aspect, the invention features, a transgenic CAIP-like, e.g., a transgenic CAIP, non-human animal, e.g., a rodent, e.g., a mouse or a rat, a rabbit, or a pig. In preferred embodiments, the transgenic animal includes (and preferably express) a heterologous form of a CAIP gene, e.g., a gene derived from humans. In other preferred embodiments, the animal has an endogenous CAIP gene which is misexpressed, e.g., a knockout. Such a transgenic animal can serve as a model for studying disorders which are related to mutated or mis-expressed CAIP alleles or for use in drug screening.

For example, the invention includes a method of evaluating the effect of the expression or misexpression of a CAIP-like gene, e.g., a CAIP gene, on any of: a parameter related to signal transduction or lymphocyte proliferation, e.g., T cell proliferation, or IL-2 production. The method includes: providing a transgenic animal having a CAIP-like transgene, e.g., a CAIP transgene, or which otherwise misexpresses a CAIP-like gene, e.g., a CAIP gene; contacting the animal with an agent, e.g., a lymphocyte inducing agent, e.g., an anti-CD3 monoclonal antibody; and evaluating the effect of the transgene on the parameter related to signal transduction or lymphocyte proliferation (e.g., by comparing the value of the parameter for a transgenic animal with the value for a control, e.g., a wild type animal).

In another aspect, the invention provides, a method of determining if a subject mammal, e.g., a primate, e.g., a human, is at risk for a disorder related to a lesion in or the misexpression of a CAIP-like family gene, e.g., a CAIP gene. Such disorders include, e.g., disorders characterized by aberrant or unwanted CD2 function, intracellular signaling, or lymphocyte proliferation, e.g., T cell proliferation. as in psoriasis. The method includes detecting, in a tissue of the subject, the presence or absence of a mutation of a CAIP-like gene, e.g., a CAIP gene, e.g., a gene encoding a protein represented by SEQ ID NO:2, or a homolog thereof. In preferred embodiments: detecting the mutation includes ascertaining the existence of at least one of: a deletion of one or more nucleotides from the gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the CAIP-like gene; (ii) exposing the probe/primer to nucleic acid of the tissue; and detecting, by hybridization, e.g., in situ hybridization, of the probe/primer to the nucleic acid, the presence or absence of the genetic lesion.

In another aspect, the invention provides, a method of determining if a subject mammal, e.g., a primate, e.g., a human, is at risk for a disorder related to a CAIP-like family gene, e.g., a CAIP gene. Such disorders including, e.g., a disorder characterized by aberrant or unwanted CD2 function, intracellular signaling, or lymphocyte proliferation, e.g., T cell proliferation as in psoriasis. The method includes detecting, in a tissue of the subject, a non-wild type level of a CAIP-like RNA or polypeptide.

In another aspect, the invention provides, a method of determining if a subject mammal, e.g., a primate, e.g., a human, is at risk for a disorder related to a lesion in or the misexpression of a CAIP-like family gene, e.g., a CAIP gene. Such disorders include, e.g., a disorder characterized by aberrant or unwanted CD2 function, intracellular signaling, or lymphocyte proliferation, e.g., T cell proliferation as in psoriasis. The method includes detecting, in a tissue of the subject, the mis-expression of a gene encoding a protein represented by SEQ ID NO:2. In preferred embodiments: detecting the misexpression includes ascertaining the existence of at least one of: an alteration in the level of a messenger RNA transcript of the gene; the presence of a non-wild type splicing pattern of a messenger RNA transcript of the gene; or a non-wild type level of the protein.

In another aspect, the invention features a method of determining, preferably prenatally, whether a subject is at risk for a disorder characterized by aberrant or unwanted level of intracellular signaling, e.g., CD2-mediated signaling, or lymphocyte proliferation, e.g., T cell proliferation. The subject can be a mammal, e.g., a human. The method includes determining the structure of a CAIP-like gene, e.g., the CAIP gene, an abnormal structure being indicative of a risk for the disorder.

In another aspect, the invention features, a method of evaluating a compound for the ability to interact with, e.g., bind, a CAIP-like family polypeptide, e.g., a CAIP polypeptide. The method includes: contacting the compound with the CAIP-like family polypeptide; and evaluating ability of the compound to interact with, e.g., to bind or form a complex with the CAIP-like family polypeptide. This method can be performed in vitro, e.g., in a cell free system, or in vivo, e.g., in a two-hybrid interaction trap assay. This method can be used to identify naturally occurring molecules which interact with CAIP-like family polypeptides. It can also be used to find natural or synthetic inhibitors of CAIP-like family polypeptides.

In another aspect, the invention features, a method of evaluating a compound, e.g., a polypeptide, e.g., a naturally occurring ligand of a CAIP-like polypeptide, e.g., a lymphocyte surface protein, e.g., a CD2 polypeptide, e.g., a fragment of a CD2 intracellular domain, or a downstream intracellular protein, or a fragment thereof, for the ability to bind a CAIP-like polypeptide. The method includes: contacting the compound with the CAIP-like polypeptide; and evaluating the ability of the compound to interact with, e.g., to bind or form a complex with the CAIP polypeptide, e.g., the ability of the compound to inhibit a CAIP polypeptide/ CD2 intracellular domain interaction. This method can be performed in vitro, e.g., in a cell free system, or in vivo, e.g., in a two-hybrid interaction trap assay. This method can be used to identify compounds, e.g., fragments or analogs of CD2, which are agonists or antagonists of CAIP.

In another aspect, the invention features, a method of evaluating a first compound, e.g., a CAIP-like polypeptide, e.g., a CAIP polypeptide, for the ability to bind a second compound, e.g., a second polypeptide, e.g., a naturally occurring ligand of CAIP-like polypeptide, e.g., a lymphocyte surface protein, e.g., a CD2 intracellular domain, or a downstream intracellular protein, or a fragment thereof. The method includes: contacting the first compound with the second compound; and evaluating the ability of the first compound to form a complex with the second compound. This method can be performed in vitro, e.g., in a cell free system, or in vivo, e.g., in a two-hybrid interaction trap assay. This method can be used to identify compounds, e.g., fragments or analogs of CAIP, which are agonists or antagonists of CAIP. In preferred embodiment, the method further includes determining whether the first compound can alter a parameter related to a CAIP-like polypeptide interaction with a ligand, e.g., a naturally occurring ligand. For example, in the case where the first compound is a CAIP polypeptide, evaluating whether a parameter related to a CAIP-CD2 interaction is altered, e.g., lymphocyte activation or IL-2 production.

In yet another aspect, the invention features a method for evaluating a compound, e.g., for the ability to modulate an interaction, e.g., the ability to inhibit an interaction of a CAIP-like family polypeptide, e.g., a CAIP polypeptide, with a second polypeptide, e.g., a polypeptide, e.g., a natural ligand of the CAIP-like polypeptide, e.g., a cell surface protein, e.g., in case of CAIP, a CD2 intracellular domain, or a downstream intracellular protein, or a fragment thereof. The method includes the steps of (i) combining the second polypeptide (or preferably a purified preparation thereof), a CAIP-like polypeptide, (or preferably a purified preparation thereof), and a compound, e.g., under conditions wherein in the absence of the compound, the second polypeptide, and the CAIP-like polypeptide, are able to interact, e.g., to bind or form a complex; and (ii) detecting the interaction, e.g., detecting the formation (or dissolution) of a complex which includes the second polypeptide, and the CAIP-like polypeptide. A change, e.g., a decrease or increase, in the formation of the complex in the presence of a compound (relative to what is seen in the absence of the compound) is indicative of a modulation, e.g., an inhibition or promotion, of the interaction between the second polypeptide, and the CAIP-like polypeptide. In preferred embodiments: the second polypeptide, and the CAIP-like polypeptide, are combined in a cell-free system and contacted with the compound; the cell-free system is selected from a group consisting of a cell lysate and a reconstituted protein mixture; the CAIP-like polypeptide, and the second polypeptide are simultaneously expressed in a cell, and the cell is contacted with the compound, e.g. in an interaction trap assay (e.g., a two-hybrid assay).

In yet another aspect, the invention features a two-phase method (e.g., a method having an in vitro, e.g., in a cell free system, and an in vivo phase) for evaluating a compound, e.g., for the ability to modulate, e.g., to inhibit or promote, an interaction of a CAIP-like family polypeptide, e.g., a CAIP polypeptide, with a second compound, e.g., a second polypeptide, e.g., a naturally occurring ligand of CAIP-like polypeptide, e.g., a lymphocyte surface protein, e.g., a CD2 intracellular domain, or a downstream intracellular protein, or a fragment thereof. The method includes steps (i) and (ii) of the method described immediately above performed in vitro, and further includes: (iii) determining if the compound modulates the interaction in vitro, e.g., in a cell free system, and if so; (iv) administering the compound to a cell or animal; and (v) evaluating the in vivo effect of the compound on an interaction, e.g., inhibition, of a CAIP-like polypeptide, e.g., CAIP, with a second polypeptide, e.g., by the effect on the intracellular signaling, e.g., a CD2-mediated intracellular signaling, or by the effect on the expression of a reporter gene.

In another aspect, the invention features a method for evaluating a compound, e.g., for the ability to modulate, e.g., to inhibit or promote, a CAIP-like polypeptide-mediated phenomenon, e.g., an aspect of intracellular signaling, or to evaluate test compounds for use as therapeutic agents. The method includes: contacting the test compound with a cell, or a cell free system, which includes a reporter gene functionally linked to a CAIP-like regulatory sequence, and detecting the modulation of the expression of the reporter gene, modulation of the expression of the reporter gene being correlated to efficacy of the compound.

In another aspect, the invention features a two-phase method (e.g., a method having a primary in vitro and a secondary in vivo phase) for evaluating a treatment. The method can be used to evaluate a treatment for the ability to modulate, e.g., to inhibit or promote, a CAIP-like polypeptide-mediated phenomenon, e.g., an aspect of intracellular signaling, or to evaluate test compounds for use as therapeutic agents. The method includes: (i) an in vitro phase in which the test compound is contacted with a cell, or a cell free system, which includes a reporter gene functionally linked to a CAIP-like regulatory sequence, and detecting the modulation of the expression of the reporter gene and (ii) if the test compound modulates the expression, administering the test compound to an animal, and evaluating the in vivo effects of the compound on a parameter related to intracellular signaling, e.g., lymphocyte activation or proliferation.

In another aspect, the invention features, a method of evaluating a compound for the ability to bind a nucleic acid encoding a CAIP-like regulatory sequence. The method includes: contacting the compound with the nucleic acid; and evaluating ability of the compound to form a complex with the nucleic acid.

In another aspect, the invention features a method of evaluating an effect of a treatment, e.g., a treatment used to treat a disorder characterized by aberrant or unwanted level of intracellular signaling, e.g., CD2-mediated signaling, or lymphocyte proliferation, e.g., T cell proliferation. The method uses a wild type test cell or organism, or a cell or organism which misexpresses a CAIP-like gene or which has a CAIP-like transgene. The method includes: administering the treatment to a test cell or organism, e.g., a cultured cell, or a mammal, and evaluating the effect of the treatment on a parameter related to an aspect of CAIP metabolism, e.g., lymphocyte activation, e.g., T cell activation, or IL-2 production. An effect on the parameter indicates an effect of the treatment. In preferred embodiments: the disorder is psoriasis or unwanted rejection of transplant tissue; the parameter is modulation of IL-2 levels or of lymphocyte activation.

In another aspect, the invention features a method of making a CAIP-like polypeptide, e.g., a CAIP polypeptide, e.g., a peptide having a non-wild type activity, e.g., an antagonist, agonist, or super agonist of a naturally occurring CAIP-like polypeptide, e.g., a naturally occurring CAIP. The method includes: altering the sequence of a CAIP-like polypeptide, e.g., altering the sequence, e.g., by substitution or deletion of one or more residues of a non-conserved region, an SH3 domain, or an SH3 binding domain, and testing the altered polypeptide for the desired activity.

In another aspect, the invention features a method of making a fragment or analog of a CAIP-like polypeptide, e.g., a CAIP polypeptide, having a biological activity of a naturally occurring CAIP-like polypeptide, e.g., a naturally occurring CAIP. The method includes: altering the sequence, e.g., by substitution or deletion of one or more residues, of a CAIP-like polypeptide, e.g., altering the sequence of a non-conserved region, an SH3 domain, or an SH3 binding domain, and testing the altered polypeptide for the desired activity.

In another aspect, the invention features a method of treating a mammal, e.g., a human, at risk for a disorder, e.g., a disorder characterized by aberrant or unwanted level of CD2 or CAIP mediated intracellular signaling, or lymphocyte proliferation, e.g., T cell proliferation. The method includes administering to the mammal a treatment, e.g., a therapeutically effective amount a CAIP encoding nucleic acid. The nucleic acid can encode an agonist of CAIP. In preferred embodiments, the disorder is a state of immunodeficiency characterized by an insufficient lymphocyte or T cell activity and an agonist is administered. In preferred embodiments, the treatment increases lymphocyte or T cell activation and thereby promotes the restoration of the immune system. The immunodeficiency can arise from any of a variety of causes, e.g., from the administration of immunosuppressive therapy, e.g., chemotherapy. In preferred embodiments, the chemotherapy is administered to treat a disorder characterized by unwanted cell proliferation, e.g., cancer.

In another aspect, the invention features a method of treating a mammal, e.g., a human, at risk for a disorder, e.g., a disorder characterized by aberrant or unwanted level of CD2 mediated intracellular signaling or lymphocyte proliferation, e.g., T cell proliferation. The method includes administering to the mammal a treatment, e.g., a therapeutically effective amount a CAIP encoding nucleic acid. The nucleic acid can encode an antagonist of CAIP, a CD2 fragment, or an intracellular protein which interacts with CAIP. In preferred embodiments the disorder is characterized by unwanted lymphocyte or T cell activation as in psoriasis or unwanted rejection of transplant tissue. In preferred embodiments, the treatment decreases lymphocyte or T cell activation.

In another aspect, the invention features a method of treating a mammal, e.g., a human, at risk for a disorder, e.g., a disorder characterized by aberrant or unwanted level of CD2 intracellular signaling or lymphocyte proliferation, e.g., T cell proliferation. The method includes administering to the mammal a treatment, e.g., a therapeutically effective amount a CAIP antisense construct, e.g., administering or in situ generating oligonucleotides or their derivatives which specifically hybridize (e.g. bind) under cellular conditions, with the cellular mRNA and/or genomic DNA encoding CAIP. In preferred embodiments the disorder is characterized by unwanted lymphocyte or T cell activation as in psoriasis or unwanted rejection of transplant tissue. In preferred embodiments, the treatment decreases lymphocyte or T cell activation.

In another aspect, the invention features a method of treating a mammal, e.g., a human, at risk for a, e.g., a disorder characterized by aberrant or unwanted level of CD2 intracellular signaling or lymphocyte proliferation, e.g., T cell proliferation. The method includes administering to the mammal a treatment, e.g., a therapeutically effective amount of a CAIP polypeptide. The polypeptide can be an agonist of CAIP. In preferred embodiments, the disorder is a state of immunodeficiency characterized by an insufficient lymphocyte or T cell activity. In preferred embodiments, the treatment increases lymphocyte or T cell activation and thereby promotes the restoration of the immune system. The immunodeficiency can arise from any of a variety of causes, e.g., from the administration of immunosuppressive therapy, e.g., chemotherapy. In preferred embodiments, the chemotherapy is administered to treat a disorder characterized by unwanted cell proliferation, e.g., cancer.

In another aspect, the invention features a method of treating a mammal, e.g., a human, at risk for a disorder, e.g., a disorder characterized by aberrant or unwanted level of CD2 intracellular signaling or lymphocyte proliferation, e.g., T cell proliferation. The method includes administering to the mammal a treatment, e.g., a therapeutically effective amount of a CAIP polypeptide,e.g., antagonist of CAIP, a CD2 fragment, or an intracellular protein which interacts with CAIP. In preferred embodiments the disorder is characterized by unwanted lymphocyte or T cell activation as in psoriasis or unwanted rejection of transplant tissue. In preferred embodiments, the treatment decreases lymphocyte or T cell activation.

In another aspect, the invention features, a human cell, e.g., a hematopoietic stem cell, transformed with a nucleic acid which encodes a CAIP-like polypeptide, e.g., a CAIP polypeptide, or transformed with a nucleic acid which encodes an antisense molecule to a CAIP-like polypeptide, e.g., a CAIP.

In another aspect, the invention includes: a CAIP-like nucleic acid, e.g., a CAIP nucleic acid inserted into a vector; a cell transformed with a CAIP-like nucleic acid, e.g., a CAIP nucleic acid; a CAIP-like polypeptide made by culturing a cell transformed with a CAIP-like nucleic acid, e.g., a CAIP nucleic acid; and a method of making a CAIP-like polypeptide including culturing a a cell transformed with a CAIP-like nucleic acid, e.g., a CAIP nucleic acid.

The CAIP-polypeptides and nucleic acids are useful for: identifying cells which preferentially express a CAIP gene, e.g., lymphocytes or cells of the testis; the production of peptides or antisense molecules which can modulate lymphocyte activation, in vivo or in vitro; for analysis of lymphocyte, e.g., CD2 mediated, activation; for the generation of anti-CAIP antibodies, which are useful for identifying cells which express CAIP or for evaluating levels of CAIP expression; for producing CAIP binding fragments of CD2, which can be used in vitro or in vivo to modulate lymphocyte activation.

Methods and compositions of the invention, e.g., agonists of CAIP, are useful for promoting the restoration of a compromised immune system. For example, a subject having a compromised immune system, e.g., an immune system compromised by the administration of immunosuppressive treatment, e.g., for the treatment of cancer, can be administered compositions of the invention which promote CD2 or CAIP-mediated lymphocyte activation.

CAIP polypeptides are useful for stimulating IL-2 production. Antagonists are useful for decreasing IL-2 production.

A "heterologous promoter", as used herein is a promoter which is not naturally associated with a gene or a purified nucleic acid.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 µg of the polypeptide; at least 1, 10, or 100 mg of the polypeptide.

"SH2 domain", as used herein, refers to a conserved apparently noncatalytic sequence of approximately 100 amino acids found in many signal transduction proteins including Fps, Stc, Abl, GAP, PLCλ, v-Crk, Nck, p85, and Vav. See Koch et al., 1991, *Science* 252:668, hereby incorporated by reference. The amino acid sequences of the SH2 domain of 27 proteins is given in Koch et al., 1991. The SH2 domain mediates protein-protein interactions between the SH2 containing protein and other proteins by recognition of a specific site on a second protein. The SH2 second protein site interaction usually results in an association of the SH2 contacting protein and the second protein.

"SH3 domain", as used herein, refers to a conserved sequence of approximately 50–52 amino acids found in many signal transduction proteins including LCK or EGFR. See, e.g., Rudd et al., 1988, *PNAS USA* 85:5192–5194; Schlessinger, 1994, *Curr. Opin. Genet & Develop.* 4:25–30, hereby incorporated by reference. The SH3 domain mediates protein-protein interactions between the SH3 containing protein and other proteins by recognition of a specific site on a second protein. The SH3/second protein site interaction usually results in an association of the SH3 contacting protein and the second protein.

A "CAIP-like SH3 domain", as used herein, refers to an SH3 domain having at least 30, 40, 42, 50, 60, 70, 80, 90, or 95% sequence similarity with one of SH3 domain 1, SH3 domain 2, or SH3 domain 3 of SEQ ID NO:2.

An "SH3 binding domain", as used herein, refers to a proline-rich sequence of about 5–20 amino acid residues in length which is active in binding to SH3 domains. The SH3 binding domains of the invention have at least 50, 60, 70, 80, or 90% homology with an SH3 binding region of SEQ ID NO:2.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

A "treatment", as used herein, includes any therapeutic treatment, e.g., the administration of a therapeutic agent or substance, e.g., a drug.

The "metabolism of a substance", as used herein, means any aspect of the, expression, function, action, or regulation of the substance. The metabolism of a substance includes modifications, e.g., covalent or non covalent modifications of the substance. The metabolism of a substance includes modifications, e.g., covalent or non covalent modification, the substance induces in other substances. The metabolism of a substance also includes changes in the distribution of the substance. The metabolism of a substance includes changes the substance induces in the structure or distribution of other substances.

A "substantially pure nucleic acid", e.g., a substantially pure DNA, is a nucleic acid which is one or both of: not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional CAIP-like sequence.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms "peptides", "proteins", and "polypeptides" are used interchangeably herein.

As used herein, the term "transgene" means a nucleic acid sequence (encoding, e.g., one or more CAIP-like polypeptides), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic animal" is any animal in which one or more, and preferably essentially all, of the cells of the animal includes a transgene. The transgene can be introduced into the cell, directly or indirectly by introduction into a precursor of the cell, by way of deliberate genetic manipulation, such as by microinjection or by infection with a recombinant virus. This molecule may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as lymphocytes, e.g., T lymphocytes. The term also covers so-called "leaky" promoters, which regulate expression of a selected DNA primarily in one tissue, but cause expression in other tissues as well.

"Unrelated to a CAIP or CAIP-like amino acid or nucleic acid sequence" means having less than 30% homology, less than 20% homology,or, preferably, less than 10% homology with a CAIP sequence disclosed herein.

"Restoration of the immune system", refers to increasing the ability of the immune system to mount a response, for example, to mount an antibody response to an antigen.

"Insufficient lymphocyte or T cell activity" refers to a condition in which the subject's immune response to an antigen is less than normal, or to a condition in which the administration of an agent which can activate lymphocytes or T cells results in an improved immune response, for example, an improved antibody response to an antigen.

A polypeptide has CAIP-like, or CAIP, biological activity if it has one, two, three, and preferably more of the following properties: (1) it can bind to the intracellular domain of a cell surface molecule, e.g., a lymphocyte cell surface molecule, e.g., in the case of the CAIP polypeptide, CD2; (2) it can bind to a downstream intracellular molecule; (3) in the case of the CAIP, it can stimulate lymphocytes; (4) in the case of the CAIP, it can stimulate IL-2 production. A polypeptide has biological activity if it is an antagonist, agonist, or super-agonist of a polypeptide having one of the above-listed properties.

"Misexpression", as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As described herein, one aspect of the invention features a pure (or recombinant) nucleic acid which includes a nucleotide sequence encoding a CAIP-like family polypeptide, and/or equivalents of such nucleic acids. The term nucleic acid as used herein can include fragments and equivalents. The term equivalent refers to nucleotide sequences encoding functionally equivalent polypeptides or functionally equivalent polypeptides which, for example, retain the ability to bind to the CD2 intracellular domain. Equivalent nucleotide sequences will include sequences that differ by one or more nucleotide substitutions, additions or deletions, such as allelic variants, and will, therefore, include sequences that differ from the nucleotide sequence of CAIP shown in SEQ ID NO:1, due to the degeneracy of the genetic code.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DETAILED DESCRIPTION OF THE INVENTION

The drawings are briefly described.

FIG. 1 is a nucleotide sequence of the YM06 clone (SEQ ID NO:1).

FIG. 2 is a map of the amino acid sequence encoded by the YM06 clone (SEQ ID NO:2). SH3 domains and SH3 binding domains (HP) are indicated.

Isolation of YM06 cDNA's

Figure 3:
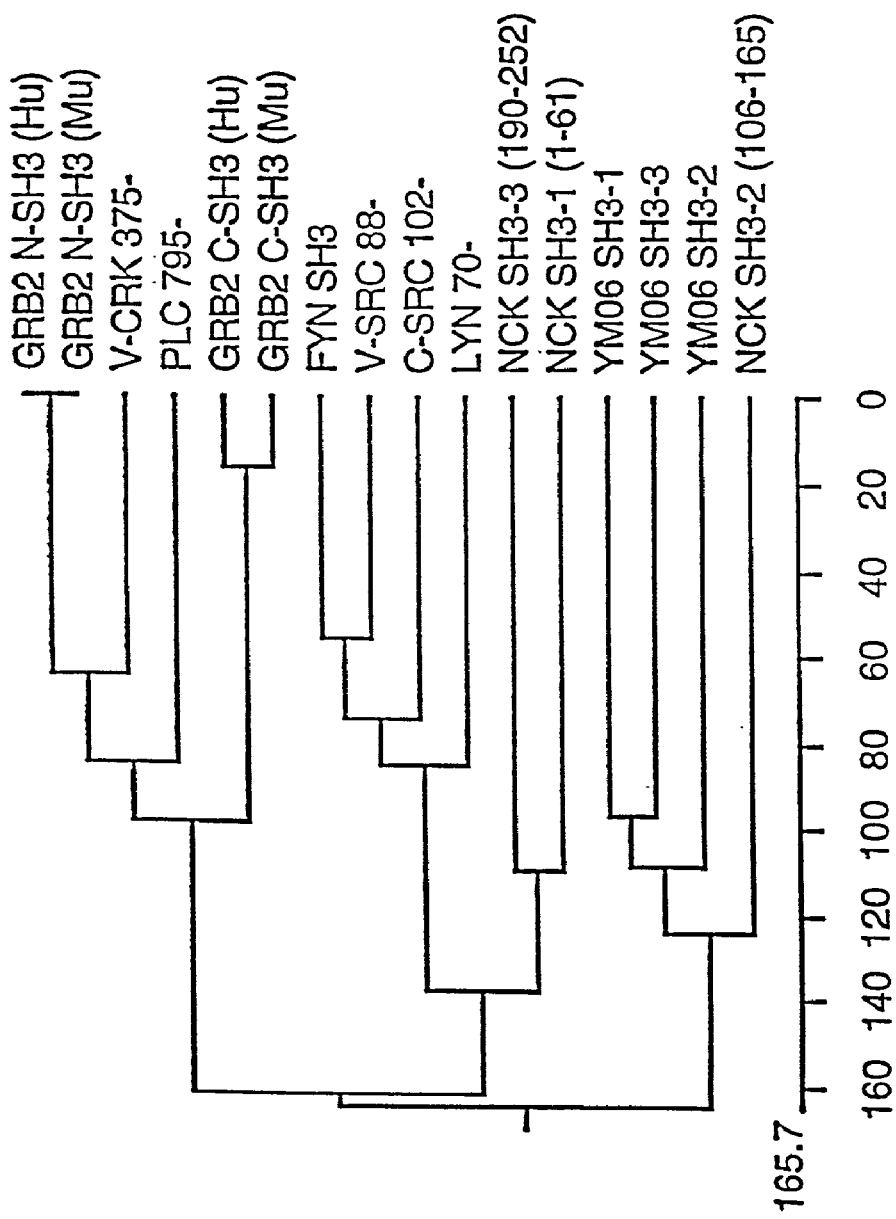
FIG. 3 is a graph depicting phylogenic analysis of different SH3 domains.

A two hybrid assay system (see e.g., Bartel et al. (1993) In *Cellular Interaction in Development: A practical Approach*, D. A. Hartley, ed., Oxford University Press, Oxford, pp. 153–179) was used to screen for proteins which specifically interact with the cytoplasmic domain of CD2. The two-hybrid system used allows for detection of protein-protein interactions in yeast cells. The known protein is often referred to as the "bait" protein. The proteins tested are often referred to as "fish" proteins. The "bait" protein is fused to the GAL4 DNA binding domain. Potential "fish" proteins are fused to the GAL4 activating domain. If the "bait" protein and a "fish" protein interact, the two GAL4 domains are brought into close proximity. In the experiments reported herein, the "bait" protein, the CD2 cytoplasmic domain, was expressed as a fusion protein with the GAL4 DNA-binding domain. The potential interacting "fish" proteins were expressed as fusion proteins with the GAL4 activating domain. The expression of a cDNA-encoded "fish" protein which is capable of interaction with the protein of interest, (the CD2 intracellular domain), allows the GAL4 activating domain fused to the "fish" protein to be brought into the vicinity of the GAL4 DNA-binding domain fused to the "bait" protein and thus renders the host capable of surviving a specific growth selection.

Two hybrid assays were performed essentially as follows. A 349 bp cDNA fragment, which contains an open reading frame of 108 amino acids of the cytoplasmic domain of CD2, was cloned into the BamH1 site of pGBT9. The insertion of this cDNA fragment was orientation specific, down-stream of, and in frame with, the GAL4 DNA-binding domain. Thus, upon transfecting the CD2 cDNA fragment into the HF7c yeast cells, the cytoplasmic domain of CD2 and the DNA-binding domain of GAL4 were expressed as a fusion protein.

An EBV-immortalized human B lymphocyte cDNA library, in the form of λ-phage, λ-ACT, was converted into pACT plasmid in *E. coli* strain BNN132 following the manufacture's protocol. The insertion of the cDNA fragments was random, downstream of, and not always in frame with the GAL4 activating domain. Therefore, upon transfection, only a fraction of the cDNA's were productively expressed as fusion proteins with the GAL4 activating domain.

The two types of hybrid plasmids described above were then co-transformed into the yeast host cells, HF7c. Co-transformants were plated on synthetic medium, lacking leucine and tryptophan, to select for those transformants that contained both plasmids. Co-transformants were also plated on synthetic medium, lacking histidine, leucine, and tryptophan, to select for colonies that expressed interacting hybrid proteins. Therefore, if the CD2 cytoplasmic domain "bait", interacted with a library-encoded protein "fish", a functional GAL4 activator was reconstituted, and the expression of the HIS3 reporter gene was activated.

Sequencing of YM06 cDNA's

Eleven cDNA clones which encoded CD2 binding proteins were identified in the two-hybrid assay. They were shown to encode proteins specific for the interaction with the cytoplasmic domain of CD2. Sequence comparison with the Genebank database, revealed that four cDNA clones contain sequences somewhat similar, but not identical, to the SH3 region of many proteins, including human growth factor receptor binding protein 2, grb2. The largest clone of the four (clone LS02-21) encompasses sequences of the other three clones.

Using LS02-21 clone as a probe, at least one message of approximately 3.4 kb was identified on a Northern blot. This indicates that either there is only one message, or if there is more than one message, the message sizes are very similar.

The 5' end 600 bp of LSO2-21 was used as a probe to screen a PHA-stimulated human PBL cDNA library. Clone YM06, containing the largest insert, was then subjected to further sequence analysis.

Structural Analysis of YM06

The relevant portion of a nucleic acid sequence of YM06 and the predicted amino acid sequence of a peptide encoded by YM06 are shown in FIGS. 1 and 2 (SEQ ID NO:1 and SEQ ID NO:2).

The predicted protein sequence shows that the three SH3 domains are coded by YM06 clone. By comparing the SH3 domains of YM06 with the known SH3 domains of other proteins, it was determined that the SH3 domain 1 (amino acids 1–47 of SEQ ID NO:2) is most likely missing the four N-terminal amino acids.

Two possibilities may explain why no consensus Kozak sequence has been identified in the YM06 clone. The first possibility is that YM06 does not contain the initiation codon at the 5' end. This is supported by the Northern blot analysis which showed a single message of approximately 3.4 kb. Thus, possibly, a fragment is missing from the YM06 cDNA clone. The second possibility is that the translation of CAIP does not use the conventional Kozak sequence. This is not uncommon; a Kozak sequence is not always identified up-stream of the initiation site in all mRNAs.

Relationship of CAIP to Other SH3 Domain-Containing Proteins

Amino acid sequence comparison was used to analyze the relationship of SH3 domains. The three SH3 domains of CAIP were found to be evolutionary quite distant from the SH3 domains of other proteins in the database. The percent identity of SH3 domains is shown in Table 1. The percent identity for the three SH3 regions of YM06 ranges from 35 to 45%. In contrast, when these SH3 domains are compared with the SH3 domains of other proteins the percent identity is on average about 26%. The only exception, the C terminal SH3 domain of human GRB2 protein, is 41% identical to SH3-2 domain of YM06. Computer assisted phylogenic analysis (FIG. 3) shows that the SH3 domains of YM06 are closer to each other than to the SH3 domains of other proteins. The MEGALIGN program used for this analysis was obtained from DNASTAR, Inc., Madison, Wis. This program relies on analyzing molecular sequences based on sequence alignments and phylogeny reconstructions (see, e.g., Dayhoff, 1978, *Atlas of Protein Sequence and Structure* 5(3):345–358; Hein, 1990, *Methods in Enzym.* 183:626–645; Saitou and Nei, 1987, *Mol. Biol. Evol.* 4(4): 406–425; Wilbur and Lipman, 1983, *PNAS USA* 80:726–730). The distribution in the phylogenic tree suggests that the SH3 domains of YM06 are evolutionarily distant from the SH3 domains of other protein. Therefore, CAIP represents a member of a family whose SH3 domains are quite distinct from the SH3 domains of known proteins.

In addition, four high proline enriched regions were identified in the carboxy-terminus of CAIP. Proline enriched regions have been suggested to interact with SH3 domains. Therefore, it is possible that the function of CAIP may involve an intramolecular interaction between the N-terminal SH3 domains of CAIP and the proline-enriched regions located at the C-terminus of CAIP or other non-CAIP molecules, e.g., CD2.

TABLE 1

% Identity of SH3 regions

| | YM06 SH3-1 | YM06 SH3-2 | YM06 SH3-3 | |
|---|---|---|---|---|
| YM06 SH3-1 | | | | |
| YM06 SH3-2 | 35 | | | |
| YM06 SH3-3 | 45 | 42 | | Average |
| GRB2 N-SH3 | 25 | 33 | 35 | 31 |
| GRB2 C-SH3 | 31 | 41 | 31 | 34 |
| NCK SH3-1 | 17 | 22 | 29 | 23 |
| NCK SH3-2 | 27 | 35 | 33 | 32 |
| NCK SH3-3 | 27 | 22 | 31 | 27 |
| PLC 795- | 26 | 34 | 26 | 29 |
| v-CRK | 18 | 27 | 35 | 27 |
| v-SRC | 18 | 20 | 27 | 22 |
| c-SRC 102- | 20 | 22 | 18 | 20 |
| FYN | 17 | 21 | 16 | 18 |
| LYN 70- | 17 | 24 | 17 | 19 |
| Average | 22 | 27 | 27 | 26 |

Expression of YM06

The CAIP RNA of YM06 was found to be expressed exclusively or preferentially in lymphocytes and testis and can thus be used to identify these tissues.

Isolation of Genomic Sequences cDNA clones isolated by a two-hybrid assay, described above, encode a mRNA sequence of the YM06 gene. On the other hand, genomic clones contain not only the protein coding sequences (divided among exons), but also intron and regulatory sequences. Methods for isolating genomic sequences are known in the art. E.g., one skilled in the art can obtain genomic sequences by making a genomic library, e.g., a recombinant DNA library which consists of a large number of recombinant DNA clones. Genomic libraries, from both human and other species, are commercially available. In order to identify clones that encode the desired nucleic acid, the library is plated out, transferred to nitrocellulose filters, and hybridizing with a labeled probe, e.g., a YM06 cDNA clone or a portion thereof. This procedure can be repeated several times until one or more clones containing the region of interest are identified.

Isolation of Other CAIP-like Family Members

One of ordinary skill in the art can apply routine methods to obtain other CAIP-like family members. For example, degenerate oligonucleotide primers can be synthesized from the regions of homology shared by more than one CAIP-like family gene, e.g., the SH3 1 domain, SH3 2 domain, or SH3 3 domain, of the previously cloned CAIP gene. The degree of degeneracy of the primers will depend on the degeneracy of the genetic code for that particular amino acid sequence used. The degenerate primers should also contain restriction endonuclease sites at the 5' end to facilitate subsequent cloning.

Total mRNA can be obtained from cells, e.g., lymphocytes, e.g., T cells, and reverse transcribed using Superscript Reverse Transcriptase Kit. Instead of an oligo(dT) primer supplied with the kit, one can use one of the 3' degenerate oligonucleotide primers to increase the specificity of the reaction. After a first strand synthesis, cDNA obtained can than be subjected to a PCR amplification using above described degenerate oligonucleotides. PCR conditions should be optimized for the annealing temperature, $Mg^{++}$ concentration and cycle duration.

Once the fragment of appropriate size is amplified, it should be Klenow filled, cut with appropriate restriction enzymes and gel purified. Such fragment can than be cloned into a vector, e.g., a Bluescript vector. Clones with inserts of appropriate size can be digested with restriction enzymes to compare generated fragments with those of other CAIP-like family members, e.g., CAIP. Those clones with distinct digestion profiles can be sequenced.

Alternatively, antibodies can be made to the conserved regions of CAIP and used to screen expression libraries.

Gene Therapy

The gene constructs of the invention can also be used as a part of a gene therapy protocol to deliver nucleic acids encoding either an agonistic or antagonistic form of a CAIP-like polypeptide, e.g., a CAIP polypeptide. The invention features expression vectors for in vivo transfection and expression of a CAIP polypeptide in particular cell types so as to reconstitute the function of, or alternatively, antagonize the function of CAIP polypeptide in a cell in which that polypeptide is misexpressed. Expression constructs of CAIP polypeptides, may be administered in any biologically effective carrier, e.g. any formulation or composition capable of effectively delivering the CAIP gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a CAIP polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc Natl. Acad. Sci. USA* 85:3014–3018; Armentano et al. (1990) *Proc. Natl. Acad. Sci. USA* 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject CAIP gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J Virol.* 51:611–619; and Flotte et al. (1993) *J Biol. Chem.* 268:3781–3790).

In addition to viral transfer methods, such as those illustrated above, non-viral methods can also be employed to cause expression of a CAIP polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject CAIP gene by the targeted cell. Exemplary gene delivery systems of this type include liposomal derived systems, poly-lysine conjugates, and artificial viral envelopes.

In a representative embodiment, a gene encoding a CAIP polypeptide can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic CAIP gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by Stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Antisense Therapy

Another aspect of the invention relates to the use of the isolated nucleic acid in "antisense" therapy. As used herein, "antisense" therapy refers to administration or in situ generation of oligonucleotides or their derivatives which specifically hybridizes (e.g. binds) under cellular conditions, with the cellular mRNA and/or genomic DNA encoding CAIP so as to inhibit expression of the encoded protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an CAIP. Alternatively, the antisense construct is an oligonucleotide probe which is generated ex vivo and which, when introduced into the cell causes inhibition of expression by hybridizing with the mRNA and/or genomic sequences of a CAIP gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included in the invention.

The compounds can be administered orally, or by transmucosal or transdermal means. For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as known in the art.

In addition to use in therapy, the oligomers of the invention may be used as diagnostic reagents to detect the presence or absence of the target DNA or RNA sequences to which they specifically bind.

The antisense constructs of the present invention, by antagonizing the normal biological activity of CAIP, can be used in the manipulation of tissue, both in vivo and in ex vivo tissue cultures.

Transgenic Animals

The invention includes transgenic animals which include cells (of that animal) which contain a CAIP transgene and which preferably (though optionally) express (or misexpress) an endogenous or exogenous CAIP gene in one or more cells in the animal. The CAIP transgene can encode the wild-type form of the protein, or can encode homologs thereof, including both agonists and antagonists, as well as antisense constructs. In preferred embodiments, the expression of the transgene is restricted to specific subsets of cells, or tissues utilizing, for example, cis-acting sequences that control expression in the desired pattern. Tissue-specific regulatory sequences and conditional regulatory sequences can be used to control expression of the transgene in certain spatial patterns. Temporal patterns of expression can be provided by, for example, conditional recombination systems or prokaryotic transcriptional regulatory sequences. In preferred embodiments, the transgenic animal carries a "knockout" CAIP-like gene, e.g., a "knockout" CAIP gene.

Genetic techniques which allow for the expression of transgenes, that are regulated in vivo via site-specific genetic manipulation, are known to those skilled in the art. For example, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject CAIP polypeptide. For example, excision of a target sequence which interferes with the expression of a recombinant CAIP gene, such as one which encodes an antagonistic homolog, can be designed to activate expression of that gene. This interference with expression of the protein can result from a variety of mechanisms, such as spatial separation of the CAIP gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

See e.g., descriptions of the crelloxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694).

Genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the recombinant CAIP gene can be regulated via control of recombinase expression.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapylike methods wherein a gene encoding the trans-activating protein, e.g. a recombinase or a prokaryotic protein, is delivered to the tissue and caused to be expressed, such as in a cell-type specific manner. By this method, the CAIP transgene could remain silent into adulthood until "turned on" by the introduction of the trans-activator.

Production of Fragments and Analogs

The inventor has discovered novel peptides that specifically interact with the CD2 intracellular domain and has provided a core physical structure having the ability to bind CD2 intracellular domain and to downstream intracellular protein. Once an example of this core structure has been provided one skilled in the art can alter the disclosed structure (of CAIP or CD2), e.g., by producing fragments or analogs, and test the newly produced structures for activity. Examples of prior art methods which allow the production and testing of fragments and analogs are discussed below. These, or analogous methods can be used to make and screen fragments and analogs of a CAIP-like polypeptide, e.g., a CAIP polypeptide, which bind CD2, or of a downstram intracellular protein. Likewise they can be used to make fragments and analogs of CAIP-like polypeptide ligands, e.g., CD2, which bind a CAIP-like polypeptide.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Production of Altered DNA and Peptide Sequences: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Production of Altered DNA and Peptide Sequences: Methods for Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765 [1978]).

Cassette Mutagenesis

Another method for preparing variants, cassette mutagenesis, is based on the technique described by Wells et al. (*Gene,* 34:315 [1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to CAIP or CD2, or to a downstream intracellular protein, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays such as the system described above (as with the other screening methods described herein), can be used to identify fragments or analogs of a CAIP polypeptide which binds to the intracellular domain of CD2. These may include agonists, superagonists, and antagonists. (The CD2 domain is used as the bait protein and the library of variants are expressed as fish fusion proteins.) In an analogous fashion, a two hybrid assay (as with the other screening methods described herein), can be used to find fragments and analogs of CD2 which bind a CAIP polypeptide.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267: 16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J Bacteriol.* 174, 4239–4245 and Klauser et al. (1990) *EMBO J* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B (Cull et al. (1992) *Proc. Natl. Acad. Sci. U.S.A.* 89:1865–1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine to perform for one skilled in the art to obtain analogs and fragments.

Peptide Mimetics

The invention also provides for reduction of the protein binding domains of the subject CAIP-like family polypeptides, e.g., a CAIP polypeptide, to generate mimetics, e.g. peptide or non-peptide agents. The peptide mimetics are able to disrupt binding of a CAIP to it's counter ligand, e.g., in the case of a CAIP polypeptide binding to a naturally occurring ligand, e.g., a CD2 intracellular domain, or a downstream intracellular protein. (The invention also includes mimetics of a CD2 peptide which block binding of CD2 to CAIP.) The critical residues of a subject CAIP polypeptide which are involved in molecular recognition of a CD2 polypeptide or of a downstream intracellular protein, can be determined and used to generate CAIP-derived peptidomimetics which competitively or noncompetatively inhibit binding of the CAIP with a CD2 polypeptide, or with a downstream intracellular protein (see, for example, "Peptide inhibitors of human papillomavirus protein binding to retinoblastoma gene protein" European patent applications EP-412,762A and EP-B31,080A). For example, scanning mutagenesis can be used to map the amino acid residues of a particular CAIP polypeptide involved in binding a CD2 polypeptide or a downstream intracellular protein, peptidomimetic compounds (e.g. diazepine or isoquinoline derivatives) can be generated which mimic those residues in binding to a CD2 polypeptide or a downstream intracellular protein, and which therefore can inhibit binding of a CAIP polypeptide to a CD2 polypeptide or to a downstream intracellular protein, and thereby interfere with the function of CAIP or CD2. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985) β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Antibodies

The invention also includes antibodies specifically reactive with a subject CAIP-like polypeptide. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject CAIP polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the CAIP polypeptides of the invention, e.g. antigenic determinants of a polypeptide of SEQ ID NO:2, or a closely related human or non-human mammalian homolog (e.g. 90 percent homologous, more preferably at least 95 percent homologous). In yet a further preferred embodiment of the present invention, the anti-CAIP antibodies do not substantially cross react (i.e. react specifically) with a protein which is: e.g., less than 80 percent homologous to SEQ ID NO:2; e.g., less than 90 percent homologous with SEQ ID NO:2; e.g., less than 95 percent homologous with SEQ ID NO:2. By "not substantially cross react", it is meant that the antibody has a binding affinity for a non-homologous protein (e.g., CD2 intracellular domain) which is less than 10 percent, more preferably less than 5 percent, and even more preferably less than 1 percent, of the binding affinity for a protein of SEQ ID NO:2. In preferred embodiments, the antibodies recognize an epitope which consists in whole or part, of residues 1–659; 1–47; 96–146; 265–317; 330–337; 359–367; 393–400; or 412–419 from SEQ ID NO:2.

The term antibody as used herein is intended to include fragments thereof which are also specifically reactive with CAIP polypeptides. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-CAIP portion.

Both monoclonal and polyclonal antibodies (Ab) directed against CAIP or CAIP variants, and antibody fragments such as Fab' and F(ab')$_2$, can be used to block the action of CAIP and allow the study of the role of a particular CAIP polypeptide of the present invention in aberrant or unwanted intracellular signaling, as well as the normal cellular function of the CAIP and CD2, e.g. by microinjection of anti-CAIP antibodies of the present invention.

Antibodies which specifically bind CAIP epitopes can also be used in immunohistochemical staining of tissue samples in order to evaluate the abundance and pattern of expression of CAIP. Anti CAIP antibodies can be used diagnostically in immuno-precipitation and immuno-blotting to detect and evaluate CAIP levels in tissue or bodily fluid as part of a clinical testing procedure. Likewise, the ability to monitor CAIP levels in an individual can allow determination of the efficacy of a given treatment regimen for an individual afflicted with such a disorder. The level of a CAIP polypeptide can be measured in cells found in bodily fluid, such as in samples of cerebral spinal fluid, or can be measured in tissue, such as produced by biopsy. Diagnostic assays using anti-CAIP antibodies can include, for example, immunoassays designed to aid in early diagnosis of CD2 or CAIP-mediated disorders, e.g., to detect cells in which a lesion of the CAIP gene has occurred.

Another application of anti-CAIP antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a subject CAIP polypeptide can then be detected with antibodies, as, for example, reacting nitrocellulose filters lifted from infected plates with anti-CAIP antibodies. Phage, scored by this assay, can then be isolated from the infected plate. Thus, the presence of CAIP homologs can be detected and cloned from other animals, and alternate isoforms (including splicing variants) can be detected and cloned from human sources.

Drug Screening Assays

By making available purified and recombinant-CAIP polypeptides, the present invention provides assays which can be used to screen for drugs which are either agonists or antagonists of the normal cellular function, in this case, of the subject CAIP polypeptides, or of their role in intracellular signaling. In one embodiment, the assay evaluates the ability of a compound to modulate binding between a CAIP polypeptide and a naturally occurring ligand, e.g., a CD2 intracellular domain, or a downstream intracellular protein. A variety of assay formats will suffice and, in light of the present inventions, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target.

Other Embodiments

The embodiments below are described with CAIP, but they can be applied to other members of the CAIP-like family.

Included in the invention are: allelic variations; natural mutants; induced mutants; proteins encoded by DNA that hybridizes under high or low stringency conditions to a nucleic acid which encodes a polypeptide of SEQ ID NO:2 (for definitions of high and low stringency see Current Protocols in Molecular Biology, John Wiley & Sons, New York, 1989, 6.3.1–6.3.6, hereby incorporated by reference); and, polypeptides specifically bound by antisera to CAIP, especially by antisera to an active site or binding domain of CAIP.

The invention also includes fragments, preferably biologically active fragments, or analogs of CAIP. A biologically active fragment or analog is one having any in vivo or in vitro activity which is characteristic of the CAIP shown in SEQ ID NO:2, or of other naturally occurring CAIP's, e.g., one or more of the biological activities described above. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Especially preferred are fragments which exist in vivo, e.g., fragments which arise from post transcriptional processing or which arise from translation of alternatively spliced RNA's. Fragments include those expressed in native or endogenous cells, e.g., as a result of post-translational processing, e.g., as the result of the removal of an amino-terminal signal sequence, as well as those made in expression systems, e.g., in CHO cells. Particularly preferred fragments are fragments, e.g., active fragments, which are generated by proteolytic cleavage or alternative splicing events. Because peptides such as CAIP often exhibit a range of physiological properties and because such properties may be attributable to different portions of the molecule, a useful CAIP fragment or CAIP analog is one which exhibits a biological activity in any biological assay for CAIP activity. Most preferably the fragment or analog possesses 10%, preferably 40%, or at least 90% of the activity of CAIP (SEQ ID NO:2), in any in vivo or in vitro CAIP assay.

Analogs can differ from naturally occurring CAIP in amino acid sequence or in ways that do not involve sequence, or both. Non-sequence modifications include in vivo or in vitro chemical derivatization of CAIP. Non-sequence modifications include changes in acetylation, methylation, phosphorylation, carboxylation, or glycosylation.

Preferred analogs include CAIP (or biologically active fragments thereof) whose sequences differ from the wild-type sequence by one or more conservative amino acid substitutions or by one or more non-conservative amino acid substitutions, deletions, or insertions which do not abolish the CAIP biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

TABLE 1-continued

CONSERVATIVE AMINO ACID REPLACEMENTS

| For Amino Acid | Code | Replace with any of |
|---|---|---|
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to a CAIP analog, will ordinarily be at least about 20 residues, more typically at least about 40 residues, preferably at least about 60 residues in length. Fragments of CAIP can be generated by methods known to those skilled in the art. The ability of a candidate fragment to exhibit a biological activity of CAIP can be assessed by methods known to those skilled in the art as described herein. Also included are CAIP polypeptides containing residues that are not required for biological activity of the peptide or that result from alternative mRNA splicing or alternative protein processing events.

In order to obtain a CAIP polypeptide, CAIP-encoding DNA can be introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-CAIP antibodies by prior art methods.

The invention claim is:

1. A method for evaluating a compound for the ability to modulate binding of a CAIP polypeptide with CD2, or a CAIP-binding fragment thereof, comprising:
   (i) combining (a) CD2, or the CAIP-binding fragment thereof, (b) a CAIP polypeptide having an amino acid sequence at least 80% identical to the sequence of SEQ ID NO:2, wherein the CAIP polypeptide is capable of binding to the intracellular domain of CD2, and (c) a compound, under conditions wherein in the absence of the compound, the CAIP polypeptide and CD2, or the CAIP-binding fragment thereof, are able to bind; and
   (ii) detecting the binding of the CAIP polypeptide and CD2, or the CAIP-binding fragment thereof, wherein a change in the binding in the presence of the compound relative to the binding in the absence of the compound is indicative of a modulation of binding.

2. The method of claim 1, wherein the compound inhibits the binding between the CAIP polypeptide and CD2, or the CAIP-binding fragment thereof.

3. The method of claim 1, wherein the combining step is performed in vitro.

4. The method of claim 3, wherein the in vitro combining step is performed in a cell free system.

5. The method of claim 3, wherein the in vitro combining step is performed in a cell lysate.

6. The method of claim 1, wherein the CAIP polypeptide is at least 90% identical to the amino acid sequence of SEQ ID NO:2.

7. The method of claim 1, wherein the CAIP polypeptide is at least 95% identical to the amino acid sequence of SEQ ID NO:2.

8. The method of claim 1, wherein the CAIP polypeptide is at least 98% identical to the amino acid sequence of SEQ ID NO:2.

9. The method of claim 1, wherein the CAIP polypeptide is at least 99% identical to the amino acid sequence of SEQ ID NO:2.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 3143 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 436...2412

(xi) SEQUENCE DESCRIPTION: SEQ ID NO: 1:

```
TGCAATAGCA AAGTACCCAC AAACCGGGTG GTACTGGGTA CTGTGGGTTG TCCCGCAGTT        60

CTGGAGGCTG GAAGTCTGAA ACTCAGATGC TGGCAGGGTT AATTTGTCCT GAGGGCTGTG       120

AGGGAGACAC AGCTCCTGGC TTTCTCCTAG CTGCTGGTAG TTTACTGGCA ACCTTTGGCA       180

TTCCTTAGCT TGTGGCATCA TCACTCCAGT ATTCATGTGA TATTCTTCCT GTGTGTGTGT       240

CTCTATGTCA AGATTTCCCC TGTTTATAAC AAAACCANTC ATATTGGGTT AGTGGTTGAG       300

CCCACCTTAC TGACCAAATA AAGTCACATG TCGAGGTACT ACGGGTTAGG ATTTCAACAT       360

GTACATTTTA GAGGGACACA ATTTAATCTA TAATAGTGTG GAATTTTCTT TTGGGTATCT       420

ACCAGTCACC AAGAT ATT TAT CCC TAC TTG ACC AGG CAC GAT GAT GAG CTN       471
            Ile Tyr Pro Tyr Leu Thr Arg His Asp Asp Glu Xaa
             1               5                      10
```

|     |     |     |     |     |     |     |     |     |     |     |     |     |     |     |     |
| --- | --- | --- | --- | --- | --- | --- | --- | --- | --- | --- | --- | --- | --- | --- | --- |
| ACG | ATC | AGC | GTG | GGT | GAA | ATC | ATC | ACC | AAC | ATC | AGG | AAG | GAG | GAT | GGA | 519 |
| Thr | Ile | Ser | Val | Gly | Glu | Ile | Ile | Thr | Asn | Ile | Arg | Lys | Glu | Asp | Gly |
|     |     | 15  |     |     |     | 20  |     |     |     |     | 25  |     |     |     |     |

| NGC | TGG | TGG | GAG | GGA | CAG | ATC | AAC | GGC | AGG | AGA | GGT | TTG | TTC | CCT | GAC | 567 |
| Xaa | Trp | Trp | Glu | Gly | Gln | Ile | Asn | Gly | Arg | Arg | Gly | Leu | Phe | Pro | Asp |
|     | 30  |     |     |     |     | 35  |     |     |     |     | 40  |     |     |     |     |

| AAC | TTT | GTA | AGA | GAA | ATA | AAG | AAA | GAG | ATG | AAG | AAA | GAC | CCT | CTC | ACC | 615 |
| Asn | Phe | Val | Arg | Glu | Ile | Lys | Lys | Glu | Met | Lys | Lys | Asp | Pro | Leu | Thr |
| 45  |     |     |     |     | 50  |     |     |     |     | 55  |     |     |     |     | 60  |

| AAC | AAA | GCT | CCA | GAA | AAG | CCC | CTG | CAC | GAA | GTG | CCC | AGT | GGA | AAC | TCT | 663 |
| Asn | Lys | Ala | Pro | Glu | Lys | Pro | Leu | His | Glu | Val | Pro | Ser | Gly | Asn | Ser |
|     |     |     |     | 65  |     |     |     |     | 70  |     |     |     |     | 75  |     |

| TTG | CTG | TCT | TCT | GAA | ACG | ATT | TTA | AGA | ACC | AAT | AAG | AGA | GGC | GAG | CGA | 711 |
| Leu | Leu | Ser | Ser | Glu | Thr | Ile | Leu | Arg | Thr | Asn | Lys | Arg | Gly | Glu | Arg |
|     |     |     | 80  |     |     |     |     | 85  |     |     |     |     | 90  |     |     |

| CGG | AGG | CGC | CGG | TGC | CAG | GTG | GCA | TTC | AGC | TAC | CTG | CCC | CAG | AAT | GAC | 759 |
| Arg | Arg | Arg | Arg | Cys | Gln | Val | Ala | Phe | Ser | Tyr | Leu | Pro | Gln | Asn | Asp |
|     |     | 95  |     |     |     |     | 100 |     |     |     |     | 105 |     |     |     |

| GAT | GAA | CTT | GAG | CTG | AAA | GTT | GGC | GAC | ATC | ATA | GAG | GTG | GTA | GGA | GAG | 807 |
| Asp | Glu | Leu | Glu | Leu | Lys | Val | Gly | Asp | Ile | Ile | Glu | Val | Val | Gly | Glu |
|     | 110 |     |     |     |     | 115 |     |     |     |     | 120 |     |     |     |     |

| GTA | GAG | GAA | GGA | TGG | TGG | GAA | GGT | GTT | CTC | AAC | GGG | AAG | ACT | GGA | ATG | 855 |
| Val | Glu | Glu | Gly | Trp | Trp | Glu | Gly | Val | Leu | Asn | Gly | Lys | Thr | Gly | Met |
| 125 |     |     |     |     | 130 |     |     |     |     | 135 |     |     |     |     | 140 |

| TTT | CCT | TCC | AAC | TTC | ATC | AAG | GAG | CTG | TCA | GGG | GAG | TCG | GAT | GAG | CTT | 903 |
| Phe | Pro | Ser | Asn | Phe | Ile | Lys | Glu | Leu | Ser | Gly | Glu | Ser | Asp | Glu | Leu |
|     |     |     |     | 145 |     |     |     |     | 150 |     |     |     |     | 155 |     |

| GGC | ATT | TCC | CAG | GAT | GAG | CAG | CTA | TCC | AAG | TCA | AGT | TTA | AGG | GAA | ACC | 951 |
| Gly | Ile | Ser | Gln | Asp | Glu | Gln | Leu | Ser | Lys | Ser | Ser | Leu | Arg | Glu | Thr |
|     |     |     | 160 |     |     |     |     | 165 |     |     |     |     | 170 |     |     |

| ACA | GGC | TCC | GAG | AGT | GAT | GGG | GGT | GAC | TCA | AGC | AGC | ACC | AAG | TCT | GAA | 999 |
| Thr | Gly | Ser | Glu | Ser | Asp | Gly | Gly | Asp | Ser | Ser | Ser | Thr | Lys | Ser | Glu |
|     |     | 175 |     |     |     |     | 180 |     |     |     |     | 185 |     |     |     |

| GGT | GCC | AAC | GGG | ACA | GTG | GCA | ACT | GCA | GCA | ATC | CAG | CCC | AAG | AAA | GTT | 1047 |
| Gly | Ala | Asn | Gly | Thr | Val | Ala | Thr | Ala | Ala | Ile | Gln | Pro | Lys | Lys | Val |
|     | 190 |     |     |     |     | 195 |     |     |     |     | 200 |     |     |     |     |

| AAG | GGA | GTG | GGC | TTT | GGA | GAC | ATT | TTC | AAA | GAC | AAG | CCA | ATC | AAA | CTA | 1095 |
| Lys | Gly | Val | Gly | Phe | Gly | Asp | Ile | Phe | Lys | Asp | Lys | Pro | Ile | Lys | Leu |
| 205 |     |     |     |     | 210 |     |     |     |     | 215 |     |     |     |     | 220 |

| AGA | CCA | AGG | TCA | ATT | GAA | GTA | GAA | AAT | GAC | TTT | CTG | CCG | GTA | GAA | AAG | 1143 |
| Arg | Pro | Arg | Ser | Ile | Glu | Val | Glu | Asn | Asp | Phe | Leu | Pro | Val | Glu | Lys |
|     |     |     |     | 225 |     |     |     |     | 230 |     |     |     |     | 235 |     |

| ACT | ATT | GGG | AAG | AAG | TTA | CCT | GCA | ACT | ACA | GCA | ACT | CCA | GAC | TCA | TCA | 1191 |
| Thr | Ile | Gly | Lys | Lys | Leu | Pro | Ala | Thr | Thr | Ala | Thr | Pro | Asp | Ser | Ser |
|     |     |     | 240 |     |     |     |     | 245 |     |     |     |     | 250 |     |     |

| AAA | ACA | GAA | ATG | GAC | AGC | AGG | ACA | AAG | AGC | AAG | GAT | TAC | TGC | AAA | GTA | 1239 |
| Lys | Thr | Glu | Met | Asp | Ser | Arg | Thr | Lys | Ser | Lys | Asp | Tyr | Cys | Lys | Val |
|     |     | 255 |     |     |     |     | 260 |     |     |     |     | 265 |     |     |     |

| ATA | TTT | CCA | TAT | GAG | GCA | CAG | AAT | GAT | GAT | GAA | TTG | ACA | ATC | AAA | GAA | 1287 |
| Ile | Phe | Pro | Tyr | Glu | Ala | Gln | Asn | Asp | Asp | Glu | Leu | Thr | Ile | Lys | Glu |
|     | 270 |     |     |     |     | 275 |     |     |     |     | 280 |     |     |     |     |

| GGA | GAT | ATA | GTC | ACT | CTC | ATC | AAT | AAG | GAC | TGC | ATC | GAC | GTA | GGC | TGG | 1335 |
| Gly | Asp | Ile | Val | Thr | Leu | Ile | Asn | Lys | Asp | Cys | Ile | Asp | Val | Gly | Trp |
| 285 |     |     |     |     | 290 |     |     |     |     | 295 |     |     |     |     | 300 |

| TGG | GAA | GGA | GAG | CTG | AAC | GGC | AGA | CGA | GGC | GTG | TTC | CCC | GAT | AAC | TTC | 1383 |
| Trp | Glu | Gly | Glu | Leu | Asn | Gly | Arg | Arg | Gly | Val | Phe | Pro | Asp | Asn | Phe |
|     |     |     |     | 305 |     |     |     |     | 310 |     |     |     |     | 315 |     |

| GTG | AAG | TTA | CTT | CCA | CCG | GAC | TTT | GAA | AAG | GAA | GGG | AAT | AGA | CCC | AAG | 1431 |
| Val | Lys | Leu | Leu | Pro | Pro | Asp | Phe | Glu | Lys | Glu | Gly | Asn | Arg | Pro | Lys |

-continued

|     |     |     |     |     | 320 |     |     |     | 325 |     |     |     | 330 |     |     |      |
|-----|-----|-----|-----|-----|-----|-----|-----|-----|-----|-----|-----|-----|-----|-----|-----|------|
| AAG | CCA | CCG | CCT | CCA | TCC | GCT | CCT | GTC | ATC | AAA | CAA | GGG | GCA | GGC | ACC | 1479 |
| Lys | Pro | Pro | Pro | Ser | Ala | Pro | Val | Ile | Lys | Gln | Gly | Ala | Gly | Thr |     |      |
|     |     | 335 |     |     |     | 340 |     |     |     | 345 |     |     |     |     |     |      |
| ACT | GAG | AGA | AAA | CAT | GAA | ATT | AAA | AAG | ATA | CCT | CCT | GAA | AGA | CCA | GAA | 1527 |
| Thr | Glu | Arg | Lys | His | Glu | Ile | Lys | Lys | Ile | Pro | Pro | Glu | Arg | Pro | Glu |      |
|     | 350 |     |     |     | 355 |     |     |     | 360 |     |     |     |     |     |     |      |
| ATG | CTT | CCA | AAC | AGA | ACA | GAA | GAA | AAA | GAA | AGA | CCA | GAG | AGA | GAG | CCA | 1575 |
| Met | Leu | Pro | Asn | Arg | Thr | Glu | Glu | Lys | Glu | Arg | Pro | Glu | Arg | Glu | Pro |      |
| 365 |     |     |     | 370 |     |     |     | 375 |     |     |     | 380 |     |     |     |      |
| AAA | CTG | GAT | TTA | CAG | AAG | CCC | TCC | GTT | CCT | GCC | ATA | CCG | CCA | AAA | AAG | 1623 |
| Lys | Leu | Asp | Leu | Gln | Lys | Pro | Ser | Val | Pro | Ala | Ile | Pro | Pro | Lys | Lys |      |
|     |     |     | 385 |     |     |     | 390 |     |     |     | 395 |     |     |     |     |      |
| CCT | CGG | CCA | CCT | AAG | ACC | AAT | TCT | CTC | AGC | AGA | CCT | GGC | GCA | CTG | CCC | 1671 |
| Pro | Arg | Pro | Pro | Lys | Thr | Asn | Ser | Leu | Ser | Arg | Pro | Gly | Ala | Leu | Pro |      |
|     |     |     | 400 |     |     |     | 405 |     |     |     | 410 |     |     |     |     |      |
| CCG | AGA | AGG | CCG | GAG | AGA | CCG | GTG | GGT | CCG | CTG | ACA | CAC | ACC | AGG | GGT | 1719 |
| Pro | Arg | Arg | Pro | Glu | Arg | Pro | Val | Gly | Pro | Leu | Thr | His | Thr | Arg | Gly |      |
|     |     | 415 |     |     |     | 420 |     |     |     | 425 |     |     |     |     |     |      |
| GAC | AGT | CCA | AAG | ATT | GAC | TTG | GCC | GGC | AGT | TCG | CTA | TCT | GGC | ATC | CTG | 1767 |
| Asp | Ser | Pro | Lys | Ile | Asp | Leu | Ala | Gly | Ser | Ser | Leu | Ser | Gly | Ile | Leu |      |
|     | 430 |     |     |     | 435 |     |     |     | 440 |     |     |     |     |     |     |      |
| GAC | AAA | GAT | CTC | TCG | GAC | CGC | AGC | AAT | GAC | ATT | GAC | TTA | GAA | GGT | TTT | 1815 |
| Asp | Lys | Asp | Leu | Ser | Asp | Arg | Ser | Asn | Asp | Ile | Asp | Leu | Glu | Gly | Phe |      |
| 445 |     |     |     | 450 |     |     |     | 455 |     |     |     | 460 |     |     |     |      |
| GAC | TCC | GTG | GTA | TCA | TCT | ACT | GAG | AAA | CTC | AGT | CAT | CCG | ACC | ACA | AGC | 1863 |
| Asp | Ser | Val | Val | Ser | Ser | Thr | Glu | Lys | Leu | Ser | His | Pro | Thr | Thr | Ser |      |
|     |     |     |     | 465 |     |     |     | 470 |     |     |     | 475 |     |     |     |      |
| AGA | CCA | AAA | GCT | ACA | GGG | AGG | CGG | CCT | CCG | TCC | CAG | TCC | CTC | ACA | TCT | 1911 |
| Arg | Pro | Lys | Ala | Thr | Gly | Arg | Arg | Pro | Pro | Ser | Gln | Ser | Leu | Thr | Ser |      |
|     |     |     | 480 |     |     |     | 485 |     |     |     | 490 |     |     |     |      |
| TCA | TCC | CTT | TCA | AGC | CCT | GAT | ATC | TTC | GAC | TCC | CCA | AGT | CCC | GAA | GAG | 1959 |
| Ser | Ser | Leu | Ser | Ser | Pro | Asp | Ile | Phe | Asp | Ser | Pro | Ser | Pro | Glu | Glu |      |
|     |     | 495 |     |     |     | 500 |     |     |     | 505 |     |     |     |     |     |      |
| GAT | AAG | GAG | GAA | CAC | ATT | TCA | CTT | GCG | CAC | AGA | GGA | GTG | GAC | GCG | TCA | 2007 |
| Asp | Lys | Glu | Glu | His | Ile | Ser | Leu | Ala | His | Arg | Gly | Val | Asp | Ala | Ser |      |
|     | 510 |     |     |     | 515 |     |     |     | 520 |     |     |     |     |     |     |      |
| AAG | AAA | ACT | TCC | AAG | ACT | GTT | ACC | ATA | TCC | CAA | GTG | TCT | GAC | AAC | AAA | 2055 |
| Lys | Lys | Thr | Ser | Lys | Thr | Val | Thr | Ile | Ser | Gln | Val | Ser | Asp | Asn | Lys |      |
| 525 |     |     |     | 530 |     |     |     | 535 |     |     |     | 540 |     |     |     |      |
| GCA | TCC | CTG | CCG | CCC | AAG | CCG | GGG | ACC | ATG | GCA | GCA | GGT | GGC | GGT | GGG | 2103 |
| Ala | Ser | Leu | Pro | Pro | Lys | Pro | Gly | Thr | Met | Ala | Ala | Gly | Gly | Gly | Gly |      |
|     |     |     | 545 |     |     |     | 550 |     |     |     | 555 |     |     |     |     |      |
| CCA | GCC | CCT | CTG | TCC | TCA | GCG | GCG | CCC | TCC | CCC | CTG | TCA | TCC | TCT | TTG | 2151 |
| Pro | Ala | Pro | Leu | Ser | Ser | Ala | Ala | Pro | Ser | Pro | Leu | Ser | Ser | Ser | Leu |      |
|     |     | 560 |     |     |     | 565 |     |     |     | 570 |     |     |     |     |     |      |
| GGA | ACA | GCT | GGA | CAC | AGA | GCC | AAC | TCC | CCG | TCT | CTG | TTC | GGC | ACG | GAA | 2199 |
| Gly | Thr | Ala | Gly | His | Arg | Ala | Asn | Ser | Pro | Ser | Leu | Phe | Gly | Thr | Glu |      |
|     |     | 575 |     |     |     | 580 |     |     |     | 585 |     |     |     |     |     |      |
| GGA | AAA | CCA | AAG | ATG | GAG | CCT | GCG | GCC | AGC | AGC | CAG | GCG | GCC | GTG | GAG | 2247 |
| Gly | Lys | Pro | Lys | Met | Glu | Pro | Ala | Ala | Ser | Ser | Gln | Ala | Ala | Val | Glu |      |
|     |     | 590 |     |     |     | 595 |     |     |     | 600 |     |     |     |     |     |      |
| GAG | CTA | AGG | ACA | CAG | GTC | CGC | GAG | CTG | AGG | AGC | ATC | ATC | GAG | ACC | ATG | 2295 |
| Glu | Leu | Arg | Thr | Gln | Val | Arg | Glu | Leu | Arg | Ser | Ile | Ile | Glu | Thr | Met |      |
| 605 |     |     |     | 610 |     |     |     | 615 |     |     |     | 620 |     |     |     |      |
| AAG | GAC | CAG | CAG | AAA | CGA | GAG | ATT | AAA | CAG | TTA | TTT | TCT | GAG | TTG | GAT | 2343 |
| Lys | Asp | Gln | Gln | Lys | Arg | Glu | Ile | Lys | Gln | Leu | Leu | Ser | Glu | Leu | Asp |      |
|     |     |     | 625 |     |     |     | 630 |     |     |     | 635 |     |     |     |     |      |
| GAA | GAG | AAG | AAA | ATC | CGG | CTT | CGG | TTG | CAG | ATG | GAA | GTG | AAC | GAC | ATA | 2391 |

-continued

```
Glu Glu Lys Lys Ile Arg Leu Arg Leu Gln Met Glu Val Asn Asp Ile
            640                 645                 650

AAG AAA GCT CTA CAA TCA AAA TGAATACTTG ATCAATGAAA TGTCACATTA        2442
Lys Lys Ala Leu Gln Ser Lys
            655

TTCATCCTGA GTCCGAGACT CAAATTTTCT GCCCCAGCCA AAATAATCTT GTGCCAAAAG   2502

ATTAAAGGTT TGCCTCAAAA TGTCCCTGTT TGAAAGATTA GCACAAAAGT CTTGATAGCA   2562

CAACACAAAT TCCATCCAAG AGGAGAATCT TCCCCAGGGT TTAGTCCTGG GGCTGGCACT   2622

CGTTGTGACT TACACAGAGC AAAATTGTGC TAAAGGCTTT TCTACTCTGA GATCTCAATG   2682

CGAAATGAAA ACTCAGGCAG TTTAGTCCAT AGTGGTACTA TTTTGATGAT ATTTTCCATT   2742

AATAAAATGT AATTTCAGAT TATTCGTTTA CAAGCTTTAT AATTTTNTGA TTTTNTAATC   2802

GTGTTTTGTC ACAGACTTCC CTAGTGTTTG TACTACACGT AGTCAGAAGC GAGTGTCCTT   2862

TTCTTTTGCT TCAGGCTAAG AGCTGCCTCG CTCTTTGTCC CCCCATTAGG ATTCTATTAC   2922

ATATGCAATT GTAGGTTCAA CCTGTCCCTT TCCCTGCCAG CAAACCCCAC CACCCTAAGA   2982

GAAATTTTAG CTTATATATG ACGGTATATT TACAAAAAGA GAAAGAGAAA ATCTGGTATT   3042

TGCAATGATC TGTGCCTTCT TTTTACCACC CTCTTGATTG GAGCTTTTGT GATGCAGCTA   3102

CCATGATTCA AAAAAATGCG GCCGCGCTCG AGCTCGAATT C                      3143
```

(2) INFORMATION FOR SEQ ID NO: 2:

(i) SEQUENCE CHARACTERISTICS:
        (A) LENGTH: 659 amino acids
        (B) TYPE: amino acid
        (D) TOPOLOGY: linear (ii) MOLECULE TYPE: protein (v) FRAGMENT TYPE: internal (ix) FEATURE:
        (B) LOCATION: 29...29
        (D) OTHER INFORMATION: where Xaa at position 29 is Arg, Cys,
            Gly, or Ser (xi) SEQUENCE DESCRIPTION: SEQ ID NO: 2:

```
Ile Tyr Pro Tyr Leu Thr Arg His Asp Asp Glu Xaa Thr Ile Ser Val
 1               5                  10                  15

Gly Glu Ile Ile Thr Asn Ile Arg Lys Glu Asp Gly Xaa Trp Trp Glu
            20                  25                  30

Gly Gln Ile Asn Gly Arg Arg Gly Leu Phe Pro Asp Asn Phe Val Arg
        35                  40                  45

Glu Ile Lys Lys Glu Met Lys Lys Asp Pro Leu Thr Asn Lys Ala Pro
    50                  55                  60

Glu Lys Pro Leu His Glu Val Pro Ser Gly Asn Ser Leu Leu Ser Ser
65                  70                  75                  80

Glu Thr Ile Leu Arg Thr Asn Lys Arg Gly Glu Arg Arg Arg Arg
            85                  90                  95

Cys Gln Val Ala Phe Ser Tyr Leu Pro Gln Asn Asp Asp Glu Leu Glu
            100                 105                 110

Leu Lys Val Gly Asp Ile Ile Glu Val Val Gly Glu Val Glu Glu Gly
        115                 120                 125

Trp Trp Glu Gly Val Leu Asn Gly Lys Thr Gly Met Phe Pro Ser Asn
    130                 135                 140

Phe Ile Lys Glu Leu Ser Gly Glu Ser Asp Glu Leu Gly Ile Ser Gln
145                 150                 155                 160
```

-continued

Asp Glu Gln Leu Ser Lys Ser Ser Leu Arg Glu Thr Thr Gly Ser Glu
                165                 170                 175

Ser Asp Gly Gly Asp Ser Ser Thr Lys Ser Glu Gly Ala Asn Gly
            180                 185                 190

Thr Val Ala Thr Ala Ala Ile Gln Pro Lys Lys Val Lys Gly Val Gly
            195                 200                 205

Phe Gly Asp Ile Phe Lys Asp Lys Pro Ile Lys Leu Arg Pro Arg Ser
            210                 215                 220

Ile Glu Val Glu Asn Asp Phe Leu Pro Val Glu Lys Thr Ile Gly Lys
225                 230                 235                 240

Lys Leu Pro Ala Thr Thr Ala Thr Pro Asp Ser Ser Lys Thr Glu Met
                245                 250                 255

Asp Ser Arg Thr Lys Ser Lys Asp Tyr Cys Lys Val Ile Phe Pro Tyr
                260                 265                 270

Glu Ala Gln Asn Asp Asp Glu Leu Thr Ile Lys Glu Gly Asp Ile Val
                275                 280                 285

Thr Leu Ile Asn Lys Asp Cys Ile Asp Val Gly Trp Trp Glu Gly Glu
    290                 295                 300

Leu Asn Gly Arg Arg Gly Val Phe Pro Asp Asn Phe Val Lys Leu Leu
305                 310                 315                 320

Pro Pro Asp Phe Glu Lys Glu Gly Asn Arg Pro Lys Lys Pro Pro Pro
                325                 330                 335

Pro Ser Ala Pro Val Ile Lys Gln Gly Ala Gly Thr Thr Glu Arg Lys
                340                 345                 350

His Glu Ile Lys Lys Ile Pro Pro Glu Arg Pro Glu Met Leu Pro Asn
                355                 360                 365

Arg Thr Glu Glu Lys Glu Arg Pro Glu Arg Glu Pro Lys Leu Asp Leu
    370                 375                 380

Gln Lys Pro Ser Val Pro Ala Ile Pro Pro Lys Lys Pro Arg Pro Pro
385                 390                 395                 400

Lys Thr Asn Ser Leu Ser Arg Pro Gly Ala Leu Pro Pro Arg Arg Pro
                405                 410                 415

Glu Arg Pro Val Gly Pro Leu Thr His Thr Arg Gly Asp Ser Pro Lys
                420                 425                 430

Ile Asp Leu Ala Gly Ser Ser Leu Ser Gly Ile Leu Asp Lys Asp Leu
                435                 440                 445

Ser Asp Arg Ser Asn Asp Ile Asp Leu Glu Gly Phe Asp Ser Val Val
    450                 455                 460

Ser Ser Thr Glu Lys Leu Ser His Pro Thr Thr Ser Arg Pro Lys Ala
465                 470                 475                 480

Thr Gly Arg Arg Pro Pro Ser Gln Ser Leu Thr Ser Ser Ser Leu Ser
                485                 490                 495

Ser Pro Asp Ile Phe Asp Ser Pro Ser Pro Glu Glu Asp Lys Glu Glu
                500                 505                 510

His Ile Ser Leu Ala His Arg Gly Val Asp Ala Ser Lys Lys Thr Ser
                515                 520                 525

Lys Thr Val Thr Ile Ser Gln Val Ser Asp Asn Lys Ala Ser Leu Pro
                530                 535                 540

Pro Lys Pro Gly Thr Met Ala Ala Gly Gly Gly Pro Ala Pro Leu
545                 550                 555                 560

Ser Ser Ala Ala Pro Ser Pro Leu Ser Ser Ser Leu Gly Thr Ala Gly
                565                 570                 575

-continued

```
His Arg Ala Asn Ser Pro Ser Leu Phe Gly Thr Glu Gly Lys Pro Lys
            580             585                 590

Met Glu Pro Ala Ala Ser Ser Gln Ala Ala Val Glu Glu Leu Arg Thr
        595             600                 605

Gln Val Arg Glu Leu Arg Ser Ile Ile Glu Thr Met Lys Asp Gln Gln
    610                 615                 620

Lys Arg Glu Ile Lys Gln Leu Leu Ser Glu Leu Asp Glu Lys Lys
625                 630                 635                 640

Ile Arg Leu Arg Leu Gln Met Glu Val Asn Asp Ile Lys Lys Ala Leu
            645                 650                 655

Gln Ser Lys
```